United States Patent [19]

Fryer et al.

[11] 4,428,879
[45] Jan. 31, 1984

[54] PYRROLO[3,4,-D][2]BENZAZEPINES

[75] Inventors: Rodney I. Fryer, North Caldwell; Eugene J. Trybulski, Parsippany; Armin Walser, West Caldwell, all of N.J.

[73] Assignee: Hoffmann-La Roche Inc., Nutley, N.J.

[21] Appl. No.: 404,787

[22] Filed: Aug. 3, 1982

Related U.S. Application Data

[60] Division of Ser. No. 286,124, Jul. 23, 1981, Pat. No. 4,354,973, which is a continuation-in-part of Ser. No. 175,555, Aug. 5, 1980, abandoned.

[51] Int. Cl.³ .............................................. C07D 487/04
[52] U.S. Cl. ................................................. 260/245.7
[58] Field of Search ..................................... 260/245.7

[56] References Cited

U.S. PATENT DOCUMENTS

| | | | |
|---|---|---|---|
| 4,022,801 | 5/1977 | Gschwend | 424/273 |
| 4,169,150 | 9/1979 | Hara et al. | 260/245.7 |
| 4,259,241 | 3/1981 | Walser | 260/245.7 |

Primary Examiner—Donald G. Daus
Assistant Examiner—William A. Teoli, Jr.
Attorney, Agent, or Firm—Jon S. Saxe; Bernard S. Leon; Frank P. Hoffman

[57] ABSTRACT

The present invention relates to compounds of the formula

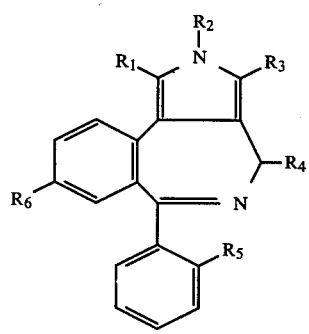

wherein $R_1$ is selected from the group consisting of hydrogen, lower alkyl, $C_3$ to $C_7$ alkenyl or alkynyl, hydroxymethyl, the group

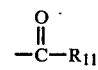

wherein $R_{11}$ is hydrogen, hydroxy, alkoxy, amino and mono- or di-lower alkylamino; and $R_3$ is selected from the group consisting of hydrogen, lower alkyl, $C_3$ to $C_7$ alkenyl or alkynyl, hydroxymethyl, the group

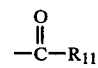

wherein $R_{11}$ is hydrogen, hydroxy, trihalomethyl, alkoxy, amino and mono- or di-lower alkylamino; $R_2$ is selected from the group consisting of hydrogen, lower alkyl, $C_3$ to $C_7$ alkenyl or alkynyl, the group

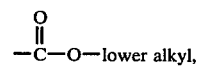

$C_2$ to $C_7$ carboxylic acids and the esters and amides thereof, hydroxy $C_2$ to $C_7$ alkyl and amino or mono- or di- lower alkyl amino $C_2$ to $C_7$ alkyl; $R_4$ is selected from the group consisting of hydrogen, acyloxy, straight chain lower alkoxy and hydroxy; $R_5$ is halogen or hydrogen; $R_6$ is halogen with the proviso that if one of $R_1$ or $R_3$ is hydroxymethyl or the group

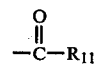

wherein $R_{11}$ is as above then the remaining substituent is selected from the group consisting of hydrogen, lower alkyl and $C_3$ to $C_7$ alkenyl or alkynyl, and $R_2$ is hydrogen and the further proviso that (A) when $R_4$ is acyloxy then $R_1$ and $R_3$ are hydrogen, lower alkyl, $C_3$ to $C_7$ alkenyl or $C_3$ to $C_7$ alkynyl, and $R_2$ is the group

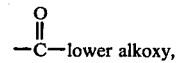

(B) when $R_4$ is hydroxy then $R_1$ and $R_3$ are hydrogen, lower alkyl, $C_3$ to $C_7$ alkenyl or $C_3$ to $C_7$ alkynyl, and $R_2$ is hydrogen or (C) when $R_4$ is alkoxy then $R_1$ and $R_3$ are hydrogen, lower alkyl, $C_3$ to $C_7$ alkenyl or $C_3$ to $C_7$ alkynyl, and the pharmaceutically acceptable salts thereof which exhibit activity as sedatives and anxiolytics.

Also disclosed are certain 5,6 dihydro derivatives, N-oxides and quarternary iminium salts of the pyrrolobenzazepines.

3 Claims, No Drawings

PYRROLO[3,4,-D][2]BENZAZEPINES

RELATED APPLICATIONS

This is a division of application Ser. No. 286,124 filed July 23, 1981 now U.S. Pat. No. 4,354,973, which is a continuation-in-part of 175,555, filed Aug. 5, 1980 now abandoned.

The compounds exhibit pharmacological activity as sedatives and anxiolytics. Also disclosed are various intermediates and processes to produce the novel end products.

DESCRIPTION OF THE INVENTION

The present invention relates to compounds of the formula

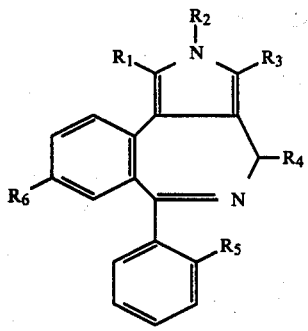

I wherein $R_1$ is selected from the group consisting of hydrogen, lower alkyl, $C_3$ to $C_7$ alkenyl or alkynyl, hydroxymethyl, the group

wherein $R_{11}$ is hydrogen, hydroxy, alkoxy, amino and mono- or di-lower alkylamino; and $R_3$ is selected from the group consisting of hydrogen, lower alkyl, $C_3$ to $C_7$ alkenyl or alkynyl, hydroxymethyl, the group

wherein $R_{11}$ is hydrogen, hydroxy, trihalomethyl, alkoxy, amino and mono- or di-lower alkylamino; $R_2$ is selected from the group consisting of hydrogen, lower alkyl, $C_3$ to $C_7$ alkenyl or alkynyl, the group

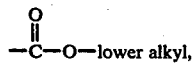

$C_2$ to $C_7$ carboxylic acids and the esters and amides thereof, hydroxy $C_2$ to $C_7$ alkyl and amino or mono- or di-lower alkyl amino $C_2$ to $C_7$ alkyl; $R_4$ is selected from the group consisting of hydrogen, acyloxy, straight chain lower alkoxy and hydroxy; $R_5$ is halogen or hydrogen; $R_6$ is halogen with the proviso that if one of $R_1$ or $R_3$ is hydroxymethyl or the group

wherein $R_{11}$ is as above then the remaining substituent is selected from the group consisting of hydrogen, lower alkyl and $C_3$ to $C_7$ alkenyl or alkynyl, and $R_2$ is hydrogen and the further proviso that (A) when $R_4$ is acyloxy then $R_1$ and $R_3$ are hydrogen, lower alkyl, $C_3$ to $C_7$ alkenyl or $C_3$ to $C_7$ alkynyl, and $R_2$ is the group

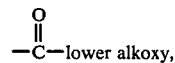

(B) when $R_4$ is hydroxy then $R_1$ and $R_3$ are hydrogen, lower alkyl, $C_3$ to $C_7$ alkenyl or $C_3$ to $C_7$ alkynyl, and $R_2$ is hydrogen or (C) when $R_4$ is alkoxy then $R_1$ and $R_3$ are hydrogen, lower alkyl, $C_3$ to $C_7$ alkenyl or $C_3$ to $C_7$ alkynyl, and the pharmaceutically acceptable salts thereof.

The compounds exhibit activity as sedative and anxiolytic agents.

By the term "halogen" or "halo" is meant bromo, chloro or fluoro except as limited herein.

By the term "lower alkyl" or "alkyl" is meant both straight and branched chain $C_1$ to $C_7$ hydrocarbon groups, preferably $C_1$ to $C_4$ carbon-hydrogen radicals, such as, methyl, ethyl, propyl, isopropyl and the like.

By the term "$C_3$ to $C_7$ alkenyl or alkynyl" there is meant $C_3$ to $C_7$ straight and branched chain hydrocarbon groups wherein at least one carbon to carbon bond is unsaturated and depicted by a double or triple bond. The point of unsaturation cannot however be between the carbon which is attached to the pyrrole ring and the next adjacent carbon, i.e., the terminal attached carbon is not unsaturated.

By the term "acyl" is meant a radical derived from an organic acid by the removal of the hydroxy goup, i.e., radicals of the formula

wherein R is $C_1$ to $C_6$ alkyl or halo alkyl, phenyl or hydrogen, e.g., acetyl, propionyl, butyryl, benzoyl, etc.

By the term "carboxylic acids and the esters and amides thereof" is meant radicals of the formula —$C_1$ to $C_6$ lower alkyl—$COR_{21}$ where $R_{21}$ is hydroxy, lower alkoxy, amino or amino which is mono- or di-substituted by lower alkyl.

Compounds of formula I wherein $R_1$ and $R_3$ are hydogen, lower alkyl, $C_3$ to $C_7$ alkenyl or $C_3$ to $C_7$ alkynyl, $R_2$ is as above but not amino or mono- or di-lower alkylamino $C_2$ to $C_7$ alkyl and $R_4$ is hydrogen can be quarternized at the imine functionality with a lower alkyl halide or sulfonate. The quarternary iminium salts thus obtained and compounds of formula I wherein $R_1$ and $R_3$ are hydrogen, lower alkyl, $C_3$ to $C_7$ alkenyl or $C_3$ to $C_7$ alkynyl and $R_4$ is hydrogen can, if desired, be reduced with appropriate reducing agents, such as, lithium aluminum hydride, sodium borohydride or sodium cyanoborohydride to afford the corresponding 5-alkyl-5,6-dihydro or 5,6-dihydro derivative compounds.

The 5,6-dihydro derivatives and the quarternary iminium salts are also active anxiolytic agents.

Compounds of formula I wherein $R_1$ and $R_3$ are hydrogen, lower alkyl, $C_3$ to $C_7$ alkenyl and $C_3$ to $C_7$ alkynyl, $R_2$ is as above but not amino or mono- or di-lower alkylamino $C_2$ to $C_7$ alkyl, $R_4$ is hydrogen and $R_5$ and $R_6$ are as above may also undergo reaction to form imine oxides and the N-oxides thereof which are also active as anxiolytic agents.

The compounds of formula I may be prepared following the schemes below:

tures range from about room temperature to 100° C. with 100° C. preferred.

III→IV

The compound of formula III is reacted with a metal hydride, such as, lithium aluminum hydride or borane in an etherial solvent such as diethyl ether or tetrahydrofuran. Reaction temperatures range from about −78° C. to room temperature with about 0° C. preferred.

IV→V

The compound of formula IV is reacted with pyridinium chlorochromate, manganese dioxide or other suit-

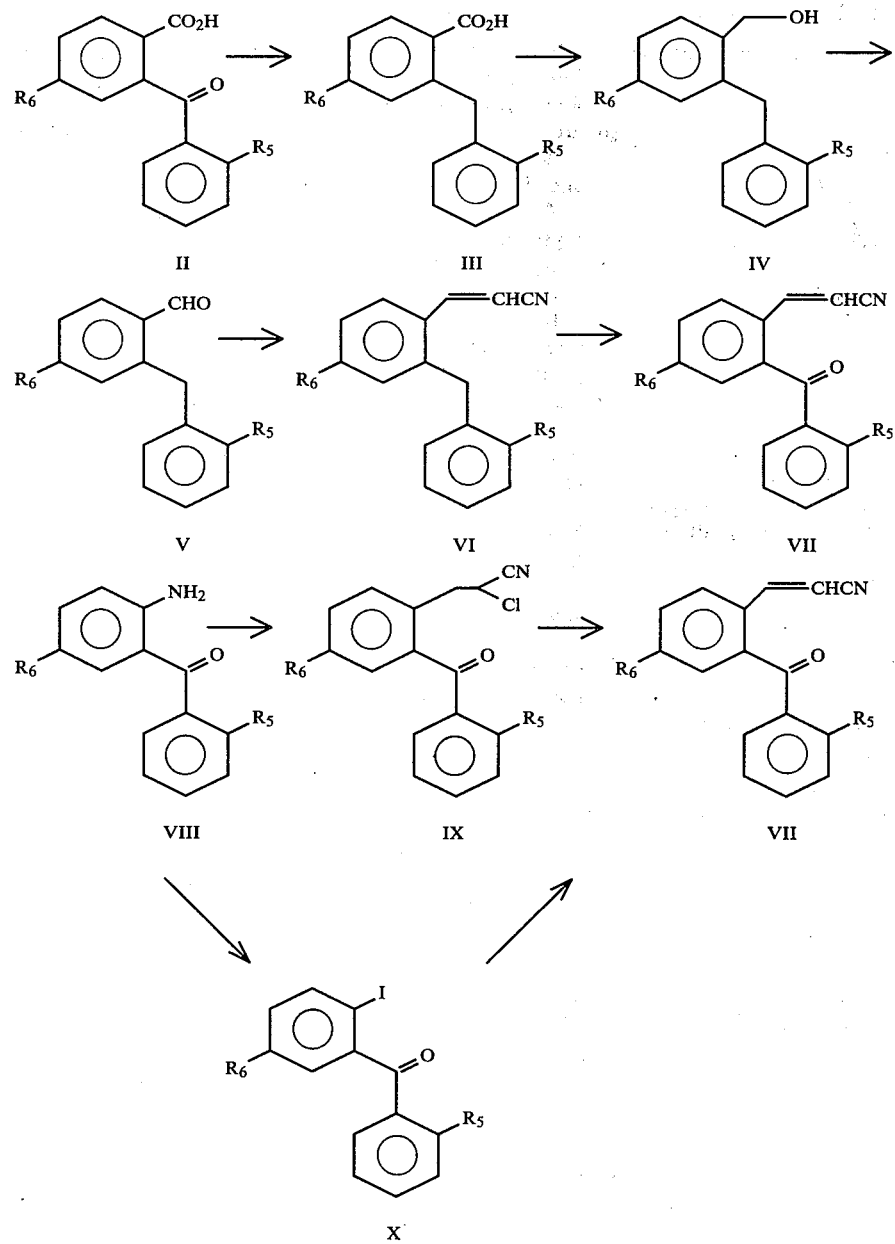

Scheme I wherein $R_5$ and $R_6$ are as above.

II→III

The compound of formula II, a well-known starting material, is reacted with zinc dust and cupric sulfate in concentrated ammonium hydroxide. Reaction temperaable oxidizing agents using methylene chloride as solvent. Reaction temperatures range from about 0° C. to the reflux temperature of the solvent with about room temperature as preferred.

V→VI

The compound of formula V is reacted with diethyl cyanomethylphosphonate in the presence of a strong base such as sodium hydride, sodium amide etc. and using an etherial solvent, such as, tetrahydrofuran. Reaction temperatures range from about 0° C. to room temperature with about room temperature preferred.

VI→VII

The compound of formula VI is reacted with chromium trioxide or an oxidizing agent derived from chromium trioxide in a mixture of acetic acid and methylene chloride. Reaction temperatures range from about 0° C. to about 90° C. with room temperature preferred.

VIII→IX

The compound of formula VIII i.e., the amino ketone is a well-known starting material. The compound is reacted with acrylonitrile in the presence of acetonitrile, a lower alkyl nitrite and cupric chloride. The reaction temperature may range from about 0° C. to about 40° C. with about room temperature as preferred.

IX→VII

The compound of formula IX above is reacted with an alkali metal, e.g., lithium, sodium or potassium carbonate and bi-carbonate mixture preferably a mixture of one part potassium carbonate to three parts potassium bicarbonate. Suitable solvents include dimethyl sulfoxide, dimethylformamide or $C_1$ or $C_4$ alcohols, e.g., methanol. Reaction temperature ranges from about 20° C. to 50° C. with room temperature preferred. The above reaction represents a dehydrohalogenation which is well-known in the art.

VIII→X

The compound of formula VIII may be diazotized using sodium nitrite in sulfuric acid and the diazonium salt may be isolated by precipitating the respective tetrafluoroborate salts. These salts are slurried in water and treated with aqueous potassium iodide at room temperature to give the iodobenzophenone X.

X→VII

The compound of formula X is reacted with acrylonitrile in the presence of a palladium II salt, such as, acetate, chloride, etc. using acetonitrile or an aromatic hydrocarbon, such as, toluene as solvent. Reaction temperatures range from about 60° C. to the reflux temperature of the solvent with reflux temperature preferred.

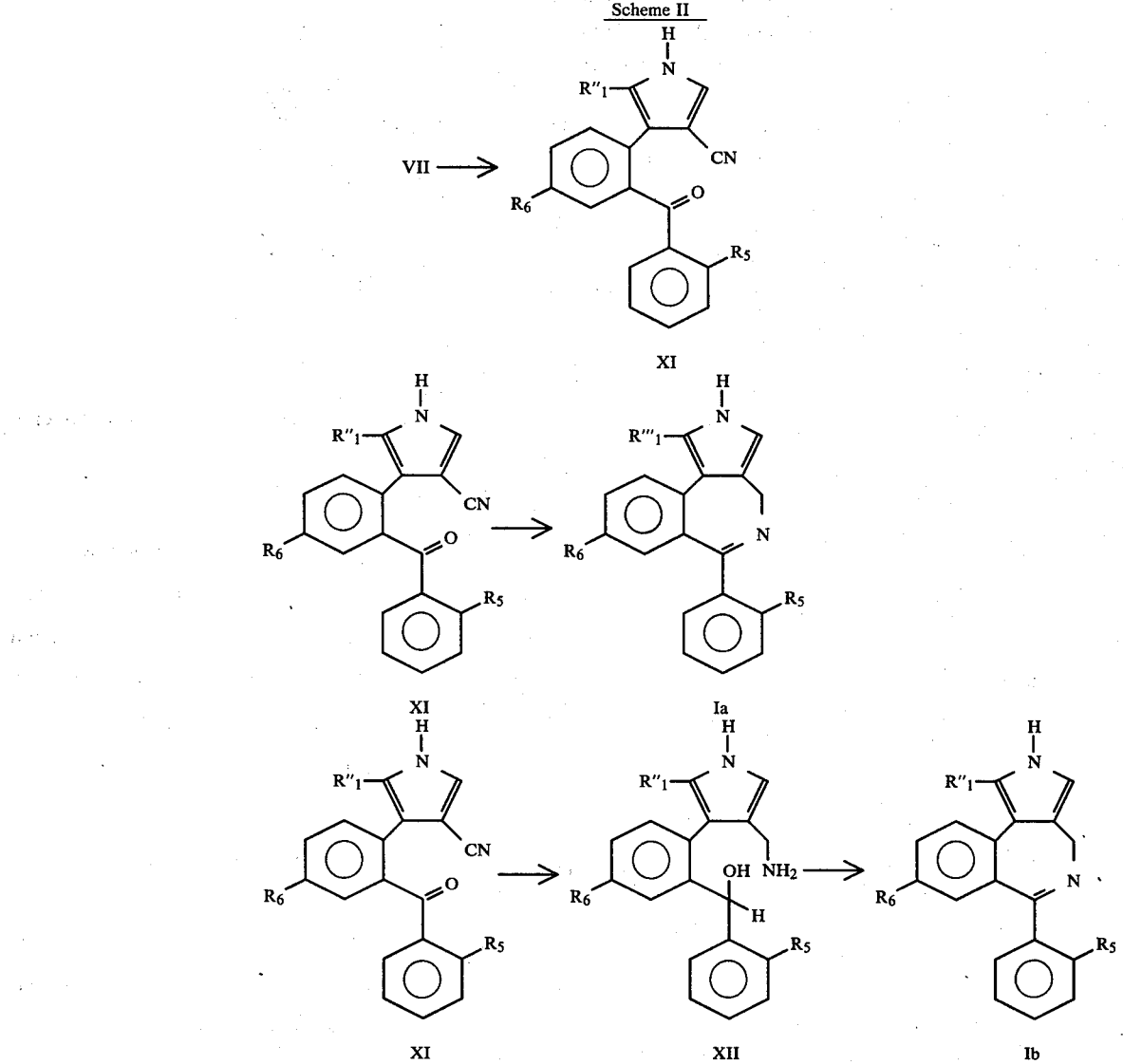

wherein $R_1''$ is hydrogen, lower alkyl, $C_3$ to $C_7$ alkenyl or alkynyl, $R_1'''$ is hydrogen or lower alkyl and $R_5$ and $R_6$ are as above.

VII→XI

The compound of formula VII is reacted with an α-tosyl alkylisocyanide, an α-tosyl $C_4$ to $C_8$ alkenyl isocyamide and an α-tosyl $C_4$ to $C_8$ alkynyl isocyamide in the presence of sodium hydride using a mixture of dimethylsulfoxide and an ether, such as, diethylether, dioxane or tetrahydrofuran as solvent. The reaction temperatures range from about 0° C. to about 40° C. with room temperature preferred. The α-tosyl isocyanides mentioned above may be prepared following the teaching of van Leusen et al., Tetrahedron Letters, 3487 (1975).

XI→Ia

The compound of formula XI is reacted with hydrogen at pressures ranging from about atmospheric pressure to five atmospheres in the presence of a transition metal catalyst, such as, Raney nickel using glacial acetic acid as solvent. The resulting amine thus formed cyclizes spontaneously to the azepine ring. Reaction temperature is about room temperature.

The first formed ring open amine is not isolated but is allowed to cyclize in situ to product Ia.

XI→XII

The compound of formula XI is reacted with a metal hydride reducing agent, such as, lithium aluminum hydride in an etherial solvent such as tetrahydrofuran. Reaction temperature ranges from about −20° C. to room temperature with 0° C. preferred.

XII→Ib

The compound of formula XII is reacted with manganese dioxide in an ether solvent, such as, tetrahydrofuran or a solvent, such as, toluene. The resulting amine thus formed cyclizes spontaneously to the azepine ring. Reaction temperature ranges from about room temperature to the boiling point of the sovent with 40° C. preferred.

Scheme III

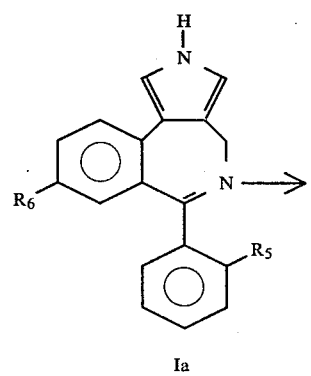

Ia

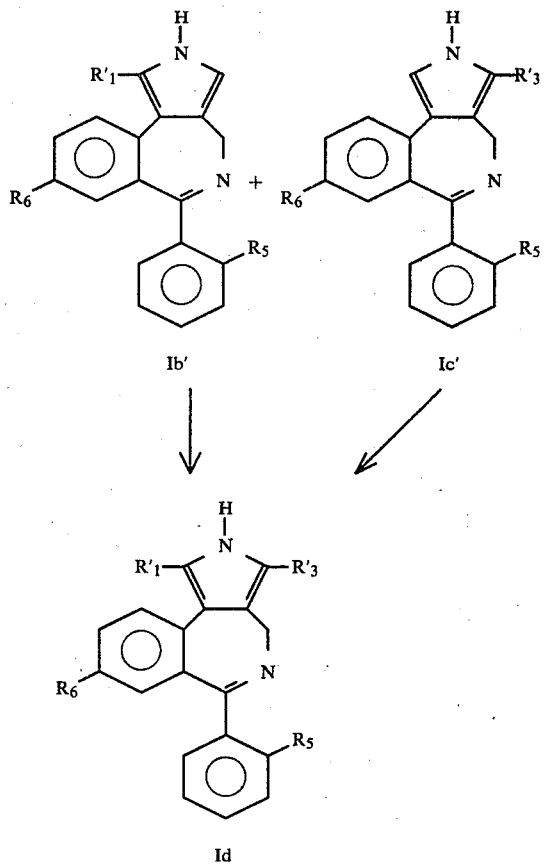

wherein $R_1'$ and $R_3'$ are lower alkyl, $C_3$ to $C_7$ alkenyl or alkynyl and $R_5$ and $R_6$ are as above, Ia→Ib'+Ic'

The compound of formula Ia is reacted with one equivalent of a strong base such as lithium diisopropylamide at between −78° C. to about 0° C. with about −20° C. preferred. The resulting anion is treated with the desired alkylating agent, such as, a lower alkyl, $C_3$ to $C_7$ alkenyl or $C_3$ to $C_7$ alkynyl halide or sulfonate. A mixture of Ib' and Ic' isomers results which can be separated by column chromatography.

Ib'→Id and Ic'→Id

The reaction conditions are the same as the conversion of Ia into Ib' and Ic'. The same or different alkylating agents may be utilized so that symmetrical or nonsymmetrical compounds may be produced.

Scheme IV
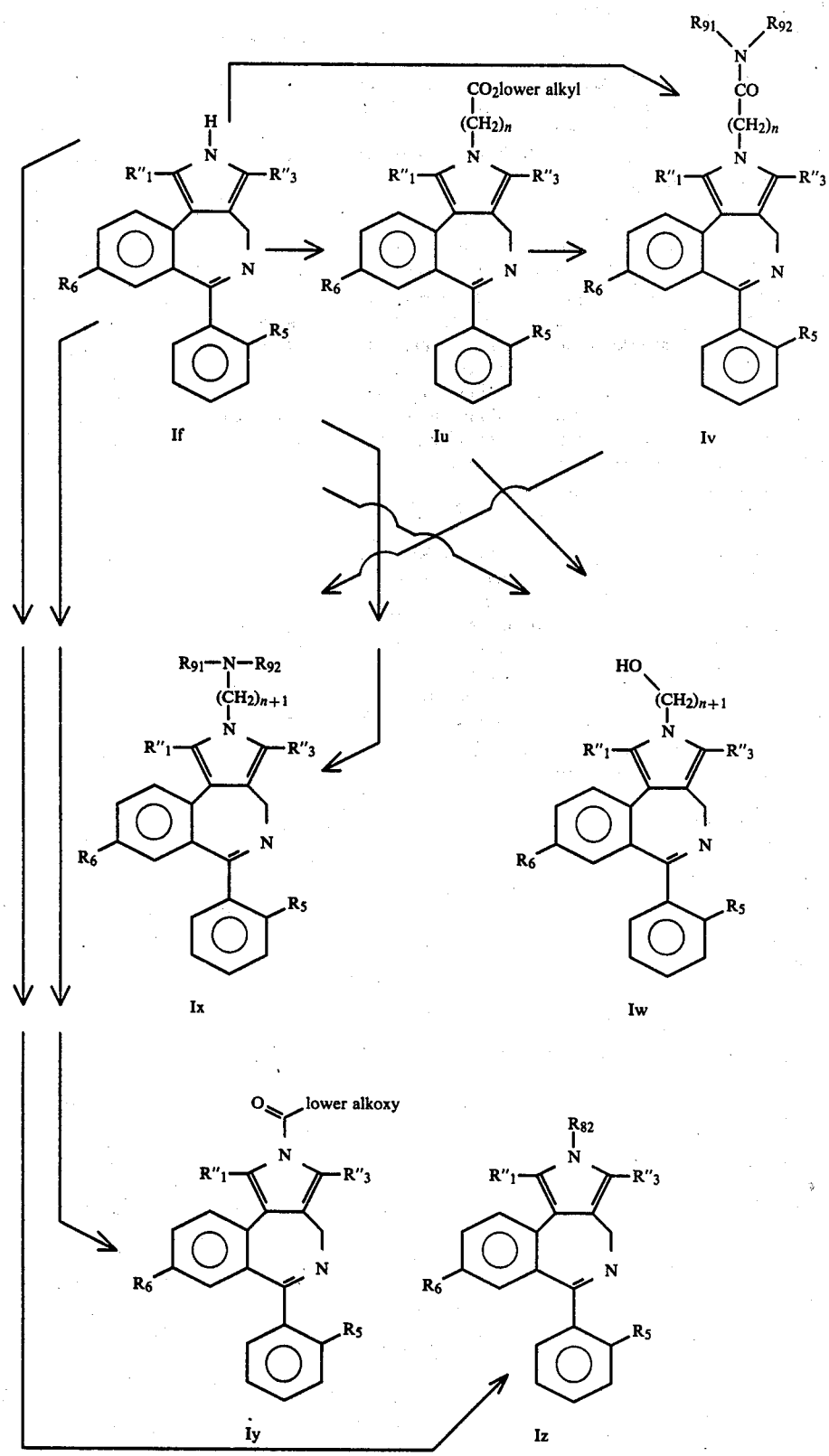
wherein $R_5$ and $R_6$ are as above, $R_1''$ and $R_3''$ are hydrogen, lower alkyl, $C_3$ to $C_7$ alkenyl or $C_3$ to $C_7$ alkynyl, n is 1 to 6, $R_{91}$ and $R_{92}$ are hydrogen or lower alkyl, $R_{82}$ is lower alkyl, $C_3$ to $C_7$ alkenyl or $C_3$ to $C_7$ alkynyl.

If→Iu

A compound of the formula If is reacted with a halo ester such as ethyl bromoacetate, ethyl 3-bromopropionate in the presence of an alkali metal alkoxide in a polar solvent such as dimethyl sulfoxide or dimethylformamide. Reaction temperature ranges from about −20° C. to room temperature with 0° C. preferred. If desired, the end product may be treated with an alkali metal carbonate or hydroxide in an aqueous ethereal solvent, such as, tetrahydrofuran. Subsequent addition of a strong mineral acid yields the corresponding carboxylic acid.

Iu→Iv

A compound of the formula Iu is reacted with ammonia or a mono- or di-substituted lower alkyl amine and a catalytic amount of its hydrochloride salt with a $C_1$ to $C_4$ alcohol solvent. The reaction is usually conducted at 100° C. using a pressure apparatus to contain the volatile reactants.

Iu→Iw

A compound of the formula Iu is reacted with a metal hydride such as lithium aluminum hydride in an etherial solvent such as tetrahydrofuran or dioxane. Reaction temperature ranges from −78° C. to room temperature with 0° C. as preferred.

If→Ix

A compound of the formula If is reacted with a compound of the formula

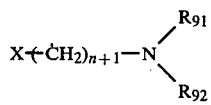

wherein $R_{91}$ and $R_{92}$ are hydrogen or lower alkyl, X is halogen and n is as above in the presence of an alkali metal alkoxide in a polar solvent such as dimethyl sulfoxide or dimethylformamide. The reaction temperature ranges from −20° C. to room temperature with room temperature preferred.

If→Iy

A compound of the formula If is reacted with an alkali metal alkoxide followed by a haloformate, such as, methyl chloroformate, benzyl chloroformate, etc. in a polar solvent, such as, dimethyl sulfoxide or dimethylformamide. The reaction temperature ranges from −20° C. to room temperature with 0° C. preferred.

If→Iz

A compound of the formula If is reacted with an alkali metal alkoxide, such as, potassium or sodium methoxide followed by an alkylating agent, or i.e., a lower alkyl, $C_3$ to $C_7$ alkenyl or $C_3$ to $C_7$ alkynyl, halide or sulfonate in a polar aprotic solvent, e.g., dimethylformamide or dimethylsulfoxide. The reaction temperature ranges from 0° C. to room temperature with 0° C. preferred.

Iv→Ix

A compound of the formula Iv is reacted with a metal hydride reducing agent, such as, lithium aluminum hydride in an ether solvent, such as, tetrahydrofuran. The reaction temperature ranges from −20° C. to room temperature with 0° C. as preferred.

If→Iw

The compound of formula If in the presence of an alkali metal alkoxide and dimethylformamide or dimethylsulfoxide is reacted with a compound of the formula

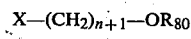

$$X-(CH_2)_{n+1}-OR_{80}$$

wherein $R_{80}$ is a hydroxy protecting group, X is halogen and n is as above.

Suitable hydroxy protecting groups include the tetrahydropyranyl ether group. Subsequent treatment with aqueous acid yields the end product.

If→Iv

The compound of formula If reacted with a compound of the formula

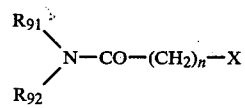

wherein $R_{91}$ and $R_{92}$ are as above, X is halogen and n is as above in the presence of an alkali metal alkoxide and dimethylformamide or dimethyl sulfoxide.

Scheme V

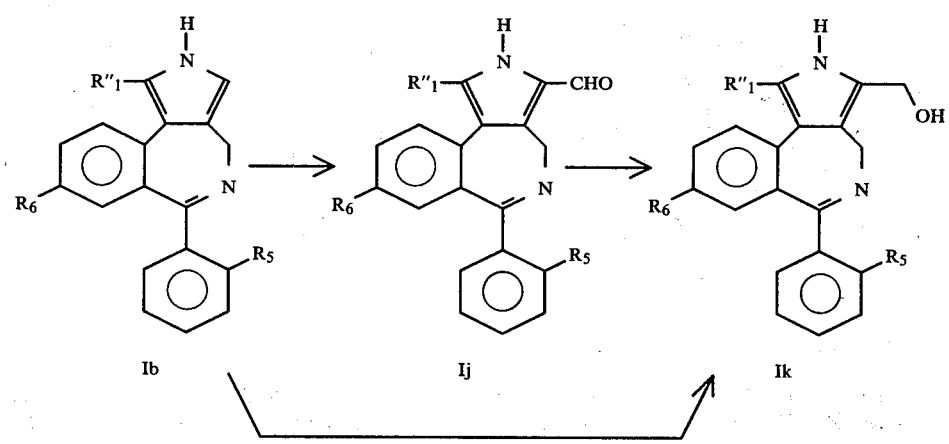

-continued

Scheme V

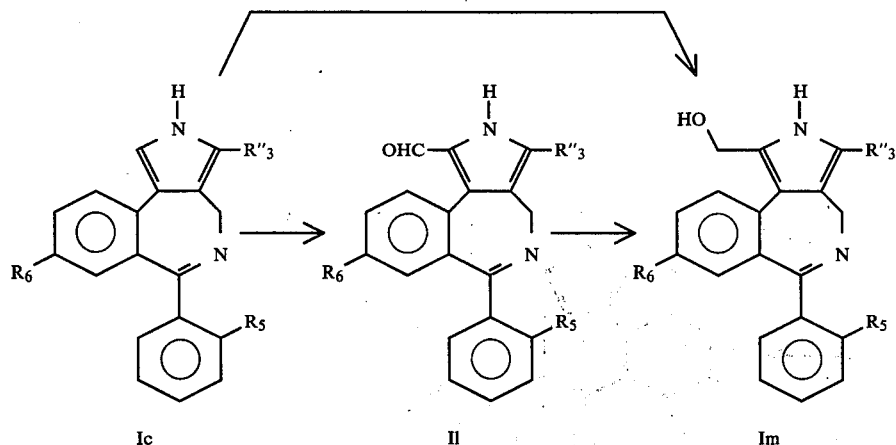

wherein $R_1''$, $R_3''$, $R_5$ and $R_6$ are as above.

Ib→Ij and Ic→Il

Compounds of the formula Ib and Ic are reacted with a mixture of dimethylformamide and phosphoryl chloride (phosgene, thionyl chloride or oxalyl chloride may also be used) with or without a solvent, such as, methylene chloride. The reaction is usually carried out at about 0° C.

Ij→Ik and Il→Im

Compounds of the formulas Ij and Il are reacted with sodium borohydride in a $C_1$ to $C_4$ alcohol with ethanol being preferred, at between −20° C. to room temperature with 0° C. preferred.

Ib→Ik and Ic→Im

Compounds of the formulas Ib and Ic are reacted with paraformaldehyde in the presence of an alkali metal carbonate in a $C_1$ to $C_4$ alcohol with methanol being preferred. Reaction temperatures range from about 0° C. to the boiling point of the solvent with room temperature preferred.

Scheme VI

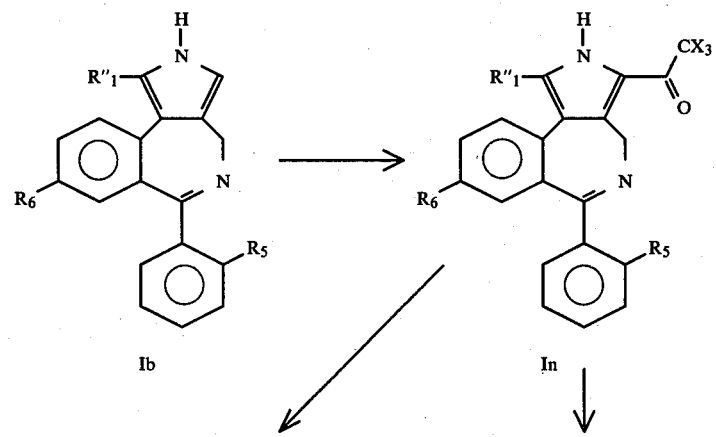

Scheme VI
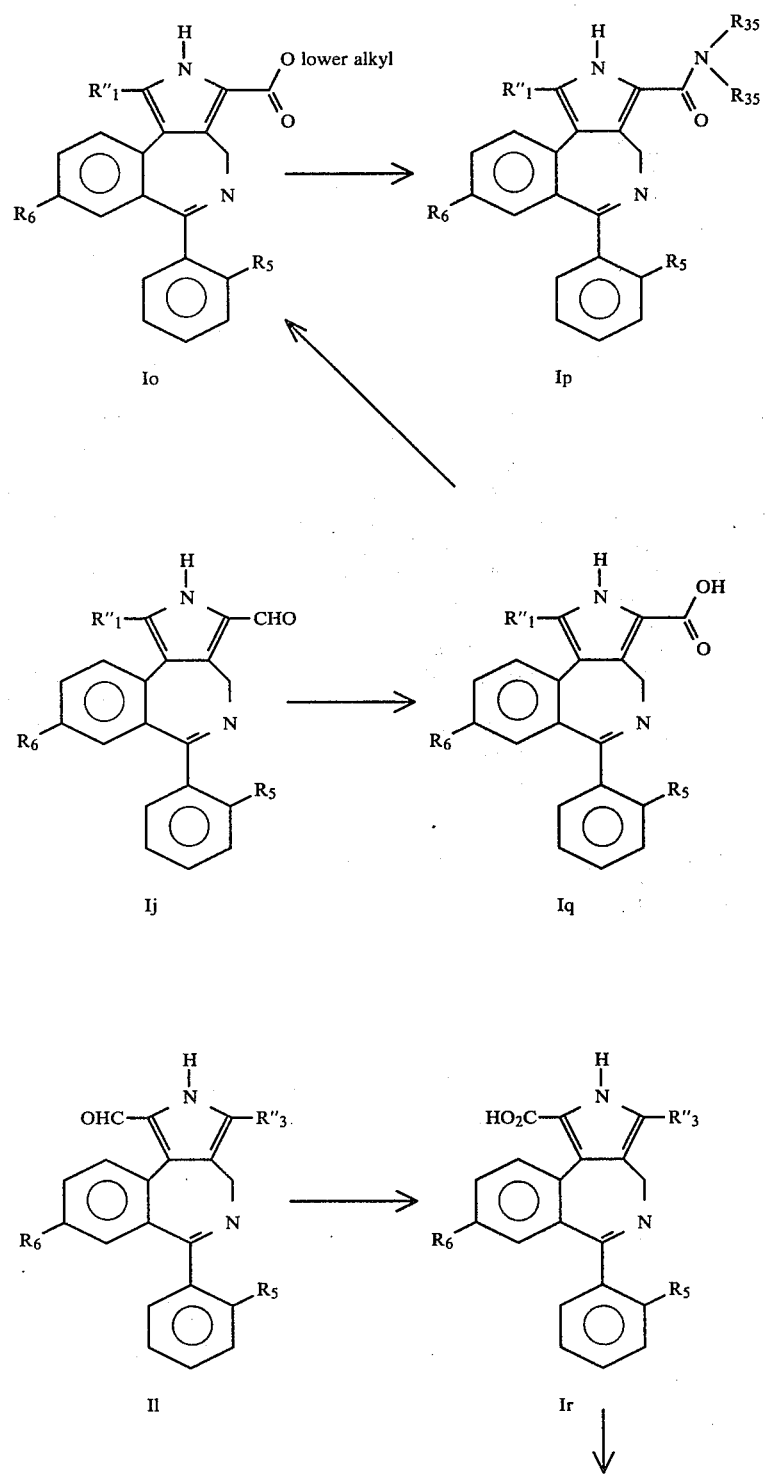

Scheme VI

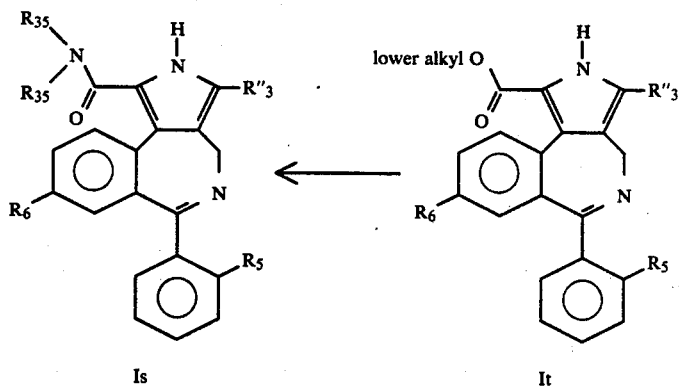

wherein $R_{35}$ is hydrogen or lower alkyl, X is halo and $R_1''$ and $R_3''$ are as above.

Ib→In

The compound of formula Ib is reacted with a trihaloacetyl halide in the presence of an inert solvent, such as, methylene chloride or diethyl ether. Reaction temperatures range from room temperature to the reflux temperature of the solvent with the reflux temperature preferred.

In→Io

The compound of formula In is reacted with the alkali metal alkoxide using the corresponding alcohol as solvent. The reaction temperature is usually between 0° C. and room temperature.

In→Ip

The compound of formula In is reacted with ammonia or the corresponding amine in a $C_1$ to $C_4$ alcohol solvent. The temperatures vary from room temperature to 100° C. with 100° C. preferred. In those cases where the reactants have boiling points lower than the reaction temperature a pressure apparatus is used to contain the reactants.

Ij→Iq and Il→Ir

Compounds of the formulas Ij or Il are reacted with potassium permanganate in a mixture of water and a water miscible inert solvent, such as, acetone, tetrahydrofuran, etc. Reaction temperatures vary from about 0° C. to 60° C. with room temperature preferred.

Iq→Io and Ir→It

Compounds of the formulas Iq and Ir are reacted with a diazoalkane such as diazomethane or diazoethane in an inert solvent such as methylene chloride or a low boiling ether, such as, diethyl ether, tetrahydrofuran, etc. The reactions are usually performed at between 0° C. and room temperature.

Compounds of the formulas Iq and Ir are alternatively dissolved in the corresponding alcohol containing a catalytic amount of strong mineral acid, such as, sulfuric acid or an organic acid such as p-toluenesulfonic acid. The reaction temperatures vary from room temperature to reflux temperature of the alcohol with room temperature preferred.

Io→Ip and It→Is

Compounds of the formulas Io and It are reacted with ammonia or a mono- or di-lower alkyl amine and a catalytic amount of their hydrochloride salts in, optionally, a $C_1$ to $C_4$ alcohol solvent. The reaction temperatures vary from room temperature to 100° C. with 100° C. as preferred. In those cases where the reactants or solvents have boiling points lower than 100° C. a pressure apparatus is used to contain the reactants.

Scheme VII

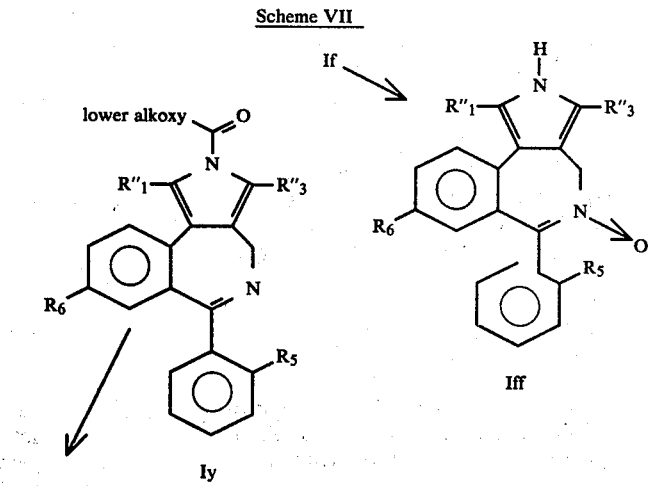

Scheme VII -continued

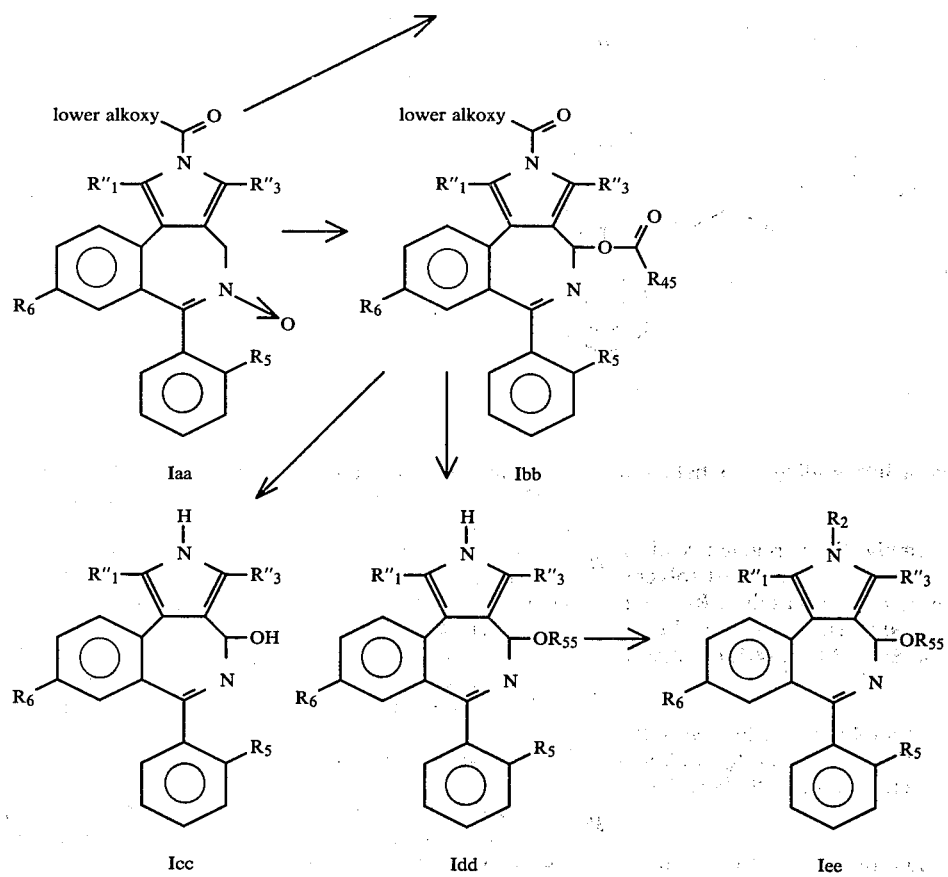

$R_{45}$ is lower alkyl or trifluoromethyl, $R_{55}$ is straight chain lower alkyl, $R_2$ is as above and $R_1''$, $R_3''$, $R_5$ and $R_6$ are as above.

Iy→Iaa

A compound of the formula Iy is reacted with a peracid such as m-chloroperoxybenzoic acid, pertifluoroacetic acid, etc. in an inert solvent such as methylene chloride. The reaction temperature ranges from 0° C. to the reflux temperature of the solvent with room temperature preferred.

Iaa→Ibb

A compound of the formula Iaa is reacted with an acid anhydride selected from suitable carboxylic acids such as acetic or trifluoroacetic anhydride. The reaction is preferably done at about the reflux temperature of the anhydride chosen however not to exceed about 130° C.

Ibb→Icc

Ibb is reacted with an alkali metal hydroxide, e.g., sodium or potassium hydroxide in an aqueous ethereal solution, e.g., a H$_2$O/dioxane or tetrahydrofuran mixture. The reaction may be run at from about 0° C. to room temperature with about room temperature as preferred.

Ibb→Idd

The compound of the formula Ibb is reacted with an alkali metal hydroxide or alkoxide, e.g., sodium or potassium hydroxide or methoxide in a mixture of a C$_1$ to C$_7$ straight chain alcohol and an ether, e.g., tetrahydrofuran or dioxane. The reaction is carried out from about 0° C. to room temperature with about 0° C. as preferred.

Idd→Iee

The compound of the formula Idd is thereafter reacted following the reaction parameters set forth in Scheme IV, i.e., steps If→Iu; If→Iv; If→Iw; Iu→Iv; Iu→Iw; If→Ix; If→Iy; If→Iz and Iv→Ix.

If→Iff

A compound of the formula If is reacted with a peracid such as m-chloroperoxybenzoic acid, pertifluoroacetic acid, etc. in an inert solvent such as methylene chloride. The reaction temperature ranges from about −20° C. to room temperature with 0° C. preferred. Furthermore it should be noted, although not shown in the above Scheme, that the compounds of formulas Iu, Iv, Iw or Iz can be reacted as above, i.e. undergo a 5-oxidation.

Iaa→Iff

The compound of the formula Iaa is reacted with an alkali metal hydroxide or carbonate, e.g., sodium hydroxide or potassium carbonate in a mixture of a C$_1$ to C$_7$ straight chain alcohol and an ether, e.g., tetrahydrofuran. The reaction is carried out from about 0° C. to the reflux temperature of the solvent with room temperature as preferred.

Scheme VIII

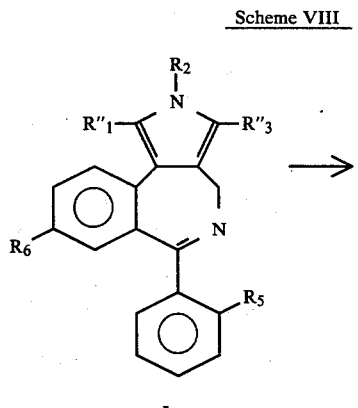

Igg

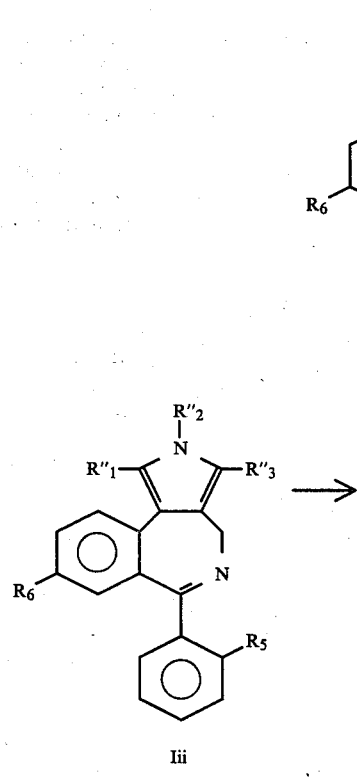

Ihh

Iii

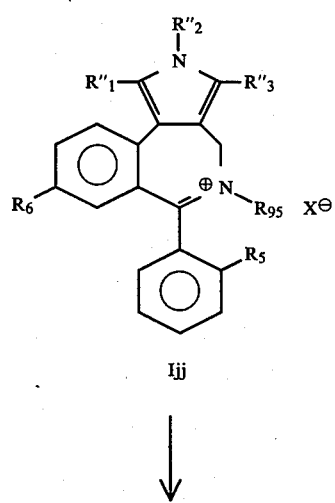

Ijj

↓

-continued
Scheme VIII

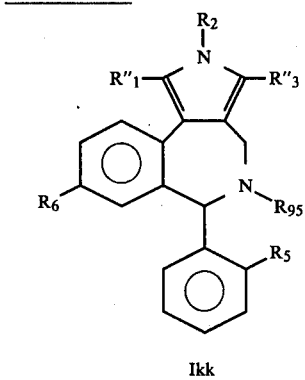

Ikk wherein $R_{95}$ is lower alkyl, $R_2''$ is equal to $R_2$ with the exception that it cannot be amino, mono- or dialkylamino $C_2$ to $C_7$ alkyl, $R_1''$, $R_2$, $R_3''$, $R_5$ and $R_6$ are as above and X is a halide or sulfonate radical.

Igg→Ihh

A compound of the formula Igg is reacted with a reducing agent, such as, sodium cyanoborohydride in a $C_1$ to $C_3$ alcohol solvent containing a mineral acid or zinc in acetic acid. The reaction temperature ranges from $-20°$ C. to room temperature with $0°$ C. preferred.

Iii→Ijj

A compound of the formula Iii is reacted with a lower alkyl halide or sulfonate in a polar aprotic solvent, such as, dimethylformamide or dimethyl sulfoxide. The reaction temperature ranges from $0°$ C. to $40°$ C. with room temperature preferred. If $R_2''$ in Iii is hydrogen and alkylation is effected in presence of base, then $R_2''$ in Ijj is equal to $R_{95}''$.

Ijj→Ikk

A compound of the formula Ijj is reacted with a reducing agent, such as, sodium borohydride or sodium cyanoborohydride in a $C_1$ to $C_3$ alcohol solvent. The reaction temperature ranges from $-20°$ C. to room temperature with room temperature preferred. In the case where $R_2''$ is $C_2$ to $C_7$ carboxylic acid amide (Iv) a stronger reducing agent, such as, lithium aluminum hydride in an ether solvent, such as, tetrahydrofuran may be used to provide a full value for $R_2$. Reaction temperature ranges from $-78°$ C. to room temperature with $0°$ C. preferred.

Compounds of formula I which are preferred are as those wherein $R_3$ is hydrogen and $R_5$ and $R_6$ are halogen, $R_1$ is hydrogen or lower alkyl, $R_2$ is as above and $R_4$ is hydrogen.

Especially preferred compounds are those of the formulas:

8-chloro-6-(2-chlorophenyl)-2H,4H-pyrrolo[3,4-d][2]benzazepine;

8-chloro-6-(2-fluorophenyl)-2H,4H-pyrrolo[3,4-d][2]benzazepine;

8-chloro-6-(2-chlorophenyl)-1-methyl-2H,4H-pyrrolo[3,4-d][2]benzazepine; and 8-chloro-6-(2-chlorophenyl)-2-methyl-2H,4H-pyrrolo[3,4-d][2]benzazepine.

8-chloro-6-(2-fluorophenyl)-2H,4H-pyrrolo[3,4-d][2]benzazepine-2-ethanol.

8-chloro-6-(2-chlorophenyl)-2H,4H-pyrrolo[3,4-d][2]benzazepine-2-carboxylic acid methyl ester.

The expression "pharmaceutically acceptable salts" is used to include salts with both inorganic and organic pharmaceutically acceptable strong acids, such as, sulfuric acid, hydrochloric acid, nitric acid, methanesulfonic acid and p-toluenesulfonic acid. Such salts can be formed quite readily by those skilled in the art with the prior art and the nature of the compound to be placed in salt form in view.

The pyrrolo[3,4-d][2]benzazepines above are useful as pharmaceuticals and are characterized by activity as sedatives and anxiolytic agents. These compounds can be used in the form of conventional pharmaceutical preparations; for example, the aforesaid compounds can be mixed with conventional organic or inorganic, inert pharmaceutical carriers suitable for parenteral or enteral administration such as for example, water gelatin, lactose, starch, magnesium stearate, talc, vegetable oil, gums, polyalkylene glycols, Vaseline or the like. They can be administered in conventional pharmaceutical forms, e.g., solid forms, for example, tablets, dragees, capsules, suppositories or the like, or in liquid forms, for example, solutions, suspensions or emulsions. Moreover, the pharmaceutical compositions containing compounds of this invention can be subjected to conventional pharmaceutical expedients such as sterilization, and can contain conventional pharmaceutical excipients such as preservatives, stabilizing agents, wetting agents, emulsifying agents, salts for the adjustment of osmotic pressure, or buffers. The compositions can also contain other therapeutically active materials.

A suitable pharmaceutical dosage unit can contain from about 1 to about 500 mg of the benzazepine end products with a dosage range of from about 1 mg to about 100 mg being the preferred oral administration and a dosage range of from about 1 mg to about 50 mg being preferred for parenteral administration. However, for any particular subject, the specific dosage regimen should be adjusted according to individual need and the professional judgment of the person administering or supervising the administration of the aforesaid compounds. It is to be understood that the dosages set forth herein are exemplary only and that they do not, to any extent, limit the scope or practice of this invention.

The term "dosage unit" as employed throughout this specification refers to pharmaceutically discrete units suitable as unitary dosages for mammalian subject each containing a predetermined quantity of active material calculated to produce the desired therapeutic effect in association with the required pharmaceutical diluent, carrier or vehicle.

The following data is indicative of the pharmacological activities of the pyrrolobenzazepines utilizing pharmacological tests well-known in the art.

| Compound | Test | | |
|---|---|---|---|
| | Footshock | Inclined Screen | Unanesthetized Cat |
| 8-chloro-6-phenyl-2H,4H—pyrrolo-[3,4-d][2]benzazepine | 25 mg/kg | 400 mg/kg | 2.5 mg/kg |
| Toxicity (LD$_{50}$) = greater than 1000 mg/kg (PO) | | | |
| 8-chloro-6-(2-chlorophenyl)-2H,4H—pyrrolo[3,4-d][2]benzazepine | 1 mg/kg | 400 mg/kg | 0.25 mg/kg |
| Toxicity (LD$_{50}$) = greater than 1000 mg/kg (PO) | | | |
| 8-chloro-6-(2-fluorophenyl)-1-methyl-2H,4H—pyrrolo[3,4-d][2]benzazepine methanesulfonate | 2 mg/kg | 400 mg/kg | 2.5 mg/kg |
| Toxicity (LD$_{50}$) greater than 1000 mg/kg (PO) | | | |

Brief description of the above tests are as follows:

Footshock

A pair of mice is confined under a one liter beaker placed on a grid which presents shock to the feet. At least 5 fighting episodes are elicited in a two-minute period. Pairs of mice are marked and pretreated 1 hour prior to a second shocking. Logarithmic dose intervals are utilized up to a maximum of 100 mg/kg. At the 100% blocking dose, 3 out of 3 pairs must be blocked from fighting.

Inclined Screen

Groups of 6 male mice are given the test drug (maximum dose of 500 mg/kg) and then are left on the inclined screen at least 4 hours for observation of paralyzing effects severe enough to cause them to slide off the screen. If activity is observed, additional doses are taken until at least two are reached at which some, but not all of the animals slide off the screen. Doses at which mice fall off the screen due to toxicity or excitation are not included in the calculation of PD$_{50}$.

Unanesthetized Cat

Cats are treated orally and observed for minimum symptoms—usually ataxia. One cat is used at a dose of 50 mg/kg. If activity is present, up to three cats/dose are used. Results are given as minimum effective dose.

The following examples are illustrative, but not limitative of this invention. All temperatures given are in degrees centigrade, unless indicated otherwise.

EXAMPLE 1

2-Benzyl-4-chlorobenzoic Acid

To a solution of 5.0 g of cupric sulfate in 3 liters of concentrated ammonium hydroxide was added 300 g (4.6 mole) of activated zinc dust and 100 g (0.42 mole) of 2-benzoyl-4-chlorobenzoic acid. The mixture was refluxed for 3 days, during which the volume was maintained by the addition of concentrated ammonium hydroxide. The mixture was cooled, and the excess zinc was removed by filtration. The filtrate was acidified by the addition of concentrated hydrochloric acid to a pH of 3. The resulting percipitate was collected by filtration, and dried to constant weight to give a white solid with mp 142°–144°.

EXAMPLE 2

2-Benzyl-4-chlorobenzyl alcohol

To a solution of 28.4 g (0.75 mole) of lithium aluminum hydride in 800 ml of ether, which was cooled to 0°, was added dropwise 85.1 g (0.345 mmole) of 2-benzyl-4-chlorobenzoic acid in 250 ml of ether. The mixture was allowed to warm to room temperature, and was stirred for 2 hr. The excess lithium alluminum hydride was discharged by the addition of 28.5 ml of water, 28.5 ml of 10% aqueous sodium hydroxide, and 85.5 ml of water. The precipitate was removed by filtration and the filtrate was dried with sodium sulfate. Removal of the ether at reduced pressure gave a colorless oil which crystallized upon standing, mp 46.5°–49°.

EXAMPLE 3

2-Benzyl-4-chlorobenzaldehyde

To a suspension of 238 g (1.1 mole) of pyridinium chlorochromate and 800 ml of methylene chloride was added 79.3 g (0.34-mole) of 2-benzyl-7-chlorobenzyl alcohol. The mixture was stirred at room temperature for 2 hr. The chromium salts were percipitated by the addition of 2.4 liters of 1:1 ether:petroleum ether, and the precipitate was removed by filtration through Celite. The solvent was removed at reduced pressure to give a yellow oil, which was used without further purification.

EXAMPLE 4

3-[2-Benzyl-4-chlorophenyl]-2-propenenitrile

To a suspension of 10.5 g (0.437 mole) of mineral oil free sodium hydride in 1.2 liters of tetrahydrofuran was added dropwise 58.4 g (0.328 mole) of diethylcyanomethyl phosphonate. After the hydrogen evolution had ceased ca 60 min, 69.4 g (0.3 mole) of 2-benzyl-4-chlorobenzaldehyde, in 75 ml of tetrahydrofuran was added dropwise. The mixture was stirred overnight at room temperature. The tetrahydrofuran solution was decanted, and concentrated at room temperature. The residue was partitioned between 2 liters of water and 1.5 liters of ether. The ether solution was separated, washed with water, and dried with sodium sulfate. The ether was removed at reduced pressure to give a yellow oil which was used without further purification.

EXAMPLE 5

3-(2-Benoyl-4-chlorophenyl)-2-propenenitrile

A mixture of 28.8 g (0.14 mole) of 3-[2-benzyl-4-chlorophenyl]-2-propenentrile, 50 g (0.5 mole) of chromium trioxide, 100 ml of methylene chloride, and 300 ml of acetic acid was stirred at room temperature overnight. The excess chromium trioxide was discharged by the slow addition of 30 ml of ethanol. The mixture was diluted with 800 ml. of water, and extracted with 500 ml of ether. The ether solution was washed with water, saturated aqueous sodium bicarbonate, and saturated aqueous sodium chloride. The ether solution was dried with anhydros sodium sulfate, and concentrated at reduced pressure to give a yellow oil which was used without further purification.

A sample of the product was purified by preparative layer chromatography (SiO₂; 2 mm; 1:1 methylene chloride: pentane) to give a white solid, mp 87°–89°.

EXAMPLE 6

4-[2-Benzoyl-4-chlorophenyl]-1H-pyrrole-3-carbonitrile

A mixture of 10.7 g (40 mmole) of 3-(2-benzoyl-4-chlorophenyl)-2-propenenitrile, 5.3 g (38 mmole) of tosylmethyl isocyanide, 75 ml of dimethyl sulfoxide and 150 ml of ether was added dropwise to a suspension of 3.7 g (77 mole) of 50% sodium hydride in mineral oil and 170 ml of ether. When the addition was complete stirring was continued for 2 hr. The mixture was diluted with water and the ether layer was separated. The aqueous solution was extracted with ether. The combined ether extracts were washed with water, dried over anhydrous sodium sulfate; and concentrated at reduced pressure to give a dark green oil. Purification by column chromatography (800 g silica gel; eluent 5% ether in methylene chloride) gave end product as off-white prisims, mp 175°–177°.

EXAMPLE 7

8-Chloro-6-phenyl-2H,4H-pyrrolo[3,4-d][2]benzazepine

A mixture of 4.0 g (13 mmole) of 4-[2-benzoyl-4-chlorophenyl]-1H-pyrrole-3-carbonitrile, 4 g of Raney nickel, and 300 ml of acetic acid were hydrogenated on a Parr apparatus for 4 hr. The Raney nickel was removed by filtration, and the filtrate was diluted with 400 ml of ice water. The acetic acid was neutralized with sodium bicarbonate, and the resulting solution extracted with methylene chloride. The methylene chloride solution was washed with water, and was dried with sodium sulfate. Concentration of the methylene chloride solution gave a yellow solid. Recrystallization from methylene chloride/ether gave a white solid, mp 203°–206°.

EXAMPLE 8

3-[2(2-Fluorobenzoyl)-4-chlorophenyl]-2-propenenitrile

The preparation of 3-[2-(2-fluorobenzoyl)-4-chlorophenyl]-2-propenenitrile was conducted in the same manner as the preparation of 3-(2-benzoyl-4-chlorophenyl)-2-propenenitrile to give off-white prisms, mp 137°–139°.

EXAMPLE 9

4-[2-(2-Fluorobenzoyl)-4-chlorophenyl]-1H-pyrrole-3-carbonitrile

The preparation of 4-[2-(2-fluorobenzoyl)-4-chlorophenyl]-1H-pyrrole-3-carbonitrile was conducted in the same manner as the preparation of 4-[2-benzoyl-4-chlorophenyl]-1H-pyrrole-3-carbonitrile to give off-white prisims, mp 177°–179°.

EXAMPLE 10

8-Chloro-6-(2-fluorophenyl)-2H,4H-pyrrolo[3,4-d][2]benzazepine

A mixture of 3.0 g (9 mmole) of 4-[2-(2-fluorobenzoyl)-4-chlorophenyl]-1H-pyrrole-3-carbonitrile, ca 3 g of Raney nickel and 150 ml of glacial acetic acid was hydrogenated on a Parr apparatus at 50 psi for 6 hr. The Raney nickel was removed by filtration, and the acetic acid was removed at reduced pressure to give a yellow oil. The yellow oil was poured over ice, basified with ammonium hydroxide and extracted with methylene chloride. The methylene chloride solution was dried over anhydrous sodium sulfate and concentrated at reduced pressure to give tan crystals. Recrystallization from a mixture of ether and methylene chloride gave cream prisms, mp 197°–199°.

EXAMPLE 11

8-Chloro-6-(2-fluorophenyl)-2H,4H-pyrrolo[3,4-d][2]benzazepine methane sulfonate The methanesulfonate salt of 8-chloro-6-(2-fluorophenyl)-2H,4H-pyrrolo[3,4-d][2]benzazepine was prepared by the addition of equimolar amounts of the benzazepine and methanesulfonic acid to methanol and by percipitating the resulting salt by the addition of ether.

Recrystallization of the salt from a mixture of methanol and ether gave orange prisms, mp 220°–221°.

EXAMPLE 12

3-[2-(2-Chlorobenzoyl)-4-chlorophenyl]-2-propenenitrile

The preparation of 3-[2-(2-chlorobenzoyl)-4-chlorophenyl]-2-propenenitrile was conducted in the same manner as the preparation of 3-(2-benzoyl-4-chlorophenyl)-2-propenenitrile to give off-white prisms, mp 137°–139°.

EXAMPLE 13

4-[2-(2-Chlorobenzoyl)-4-chlorophenyl]-1H-pyrrole-3-carbonitrile

The preparation of 4-[2-(2-chlorobenzoyl)-4-chlorophenyl]-1H-pyrrole-3-carbonitrile was conducted in the same manner as the preparation of 4-[2-benzoyl-4-chlorophenyl]-1H-pyrrole-3-carbonitrile to give off-white prisms, mp 182°–184°.

EXAMPLE 14

8-Chloro-6-(2-chlorophenyl)-2H,4H-pyrrolo[3,4-d][2]benzazepine

The preparation of 8-chloro-6-(2-chlorophenyl)-2H,4H-pyrrolo[3,4-d][2]benzazepine was conducted in the same manner as the preparation of 8-chloro-6-(2-fluorophenyl)-2H,4H-pyrrolo[3,4-d][2]benzazepine to give cream prisms, mp 204°–206°.

EXAMPLE 15

8-Chloro-6-(2-chlorophenyl)-2H,4H-pyrrolo[3,4-d][2]benzazepine methane sulfonate The methanesulfonate salt of 8-chloro-6-(2-chlorophenyl)-2H,4H-pyrrolo[3,4-d][2]benzazepine was prepared by the addition of equimolar amounts of the benzazepine and methanesulfonic acid to methanol and by precipitating the resulting salt by the addition of ether. Recrystallization of the salt from a mixture of methanol and ether gave orange prisms, mp 239°–241°.

EXAMPLE 16

4-[2-(2-Fluorobenzoyl)-4-chlorophenyl]-5-methyl-1H-pyrrole-3-carbonitrile

A mixture of 34.5 g (121 mmole) of 3-[2-(2-fluorobenzoyl)-4-chlorophenyl]-2-propenenitrile, 25.3 g (121 mmole) of 1-tosylethyl isocyanide, 200 ml of dimethyl sulfoxide and 400 ml of ether was added dropwise to a suspension of 8.9 g (184 mmole) of 50% sodium hydride in mineral oil and 450 ml of ether. When the addition was complete stirring was continued for 2 hr. The mixture was diluted with water and the ether layer was separated. The aqueous solution was extracted with ether. The combined ether extracts were washed with water, dried over anhydrous sodium sulfate, and concentrated at reduced pressure to give a dark oil. Crystallization from ether gave off-white crystals. A small portion was recrystallized from a mixture of methylene chloride and ether to give colorless prisms, mp 201°–202°.

EXAMPLE 17

8-Chloro-6-(2-fluorophenyl)-1-methyl-2H,4H-pyrrolo[3,4-d][2]benzazepine

The preparation of 8-chloro-6-(2-fluorophenyl)-1-methyl-2H,4H-pyrrolo[3,4-d][2]benzazepine was conducted in the same manner as the preparation of 8-chloro-6-(2-fluorophenyl)-2H,4H-pyrrolo[3,4-d][2]benzazepine to give colorless prisms, mp 226°–227°.

EXAMPLE 18

8-Chloro-6-(2-fluorophenyl)-1-methyl-2H,4H-pyrrolo[3,4-d][2]benzazepine methanesulfonate The methanesulfonate salt of 8-chloro-6-(2-fluorophenyl)-1-methyl-2H,4H-pyrrolo[3,4-d][2]benzazepine was prepared by the addition of equimolar amounts of the benzazepine and methanesulfonic acid to methanol and isolated by precipitating the salt by the addition of ether. Recrystallization of the salt from a mixture of methanol and ether gave orange prisms, mp 259°–261°.

EXAMPLE 19

8-Chloro-6-phenyl-2H,4H-pyrrolo[3,4-d][2]benzazepine-1-carboxaldehyde and
8-Chloro-6-phenyl-4H-pyrrole[3,4-d][2]benzazepine-3-carboxaldehyde Phosphorous oxychloride, 0.6 ml, was added to a solution of 0.6 g (2.05 mmol) of 8-chloro-6-phenyl-2H,4H-pyrrolo[3,4-d][2]benzazepine in 8 ml of the dimethylformamide cooled in ice-water. The mixture was stirred for 1 hr with cooling and was then poured into 10% aqueous sodium carbonate solution. The precipitated product was collected and dissolved in methylene chloride. The solution was dried and evaporated. The residue (0.55 g) was chromatographed over silica gel using 20% (v/v) of ethyl acetate in methylene chloride for elution. The less polar 3-carboxaldehyde was crystallized from ether and recrystallized from ethyl acetate/hexane, mp 225°–226°.

EXAMPLE 20

8-Chloro-6-phenyl-2H,4H-pyrrolo[3,4-d][2]benzazepine-3-methanol and
8-chloro-6-phenyl-2H,4H-pyrrolo[3,4-d][2]benzazepine-1-methanol Phosphorous oxychloride, 5 ml, was added to a solution of 3 g (0.013 mole) of 8-chloro-6-phenyl-2H,4H-pyrrolo[3,4-d][2]benzazepine in 40 ml of dimethylformamide cooled in ice-water. After stirring and cooling for 1 hr, the reaction mixture was poured into 10% aqueous sodium carbonate solution. The precipitated product was collected and dissolved in methylene chloride. The solution was dried and evaporated and the residue was dissolved in 100 ml of ethanol. Following the addition of 0.8 g of sodium borohydride the mixture was stirred at room temperature for 30 min. The solvent was partially evaporated under reduced pressure and the remainder was partitioned between methylene chloride and water. The organic layer was dried and evaporated and the residue was chromatographed over 250 g of silica gel using methylene chloride/ethyl acdtate 2:3.

The first eluted 8-chloro-6-phenyl-2H,4H-pyrrolo[3,4-d][2]benzazepine-1-methanol was crystallized from ethyl acetate to yield off-white crystals with mp 208°–210°.

The more polar 8-chloro-6-phenyl-4H-pyrrolo[3,4-d][2]benzazepine-3-methanol was crystallized from ethyl acetate and yielded off-white crystals with mp 216°–218°.

EXAMPLE 21

8-Chloro-6-phenyl-2H,4H-pyrrolo[3,4-d][2]benzazepine-2-acetic acid ethyl ester

To a solution of 1.4 g (12.4 mmole) of potassium t-butoxide in 30 ml of dry dimethylformamide was added 2.4 g (8.2 mmole) of 8-chloro-6-phenyl-2H,4H-pyrrolo[3,4-d][2]benzazepine. The mixture was cooled to 0°, and stirred for 10 min. To the mixture was added 1.3 mol (11.7 mmole) of ethyl bromoacetate. The mixture was stirred at 0° for 45 min, diluted with water, and extracted with ether. The ether solution was washed with water, dried with sodium sulfate, and concentrated at reduced pressure to give a yellow oil. Purification by column chromatography (70 g SiO$_2$, 9:1 methylene chloride/ether) gave as the first major component a yellow oil.

A second component consisted of recovered starting material mp 202°–204°.

EXAMPLE 22

8-Chloro-6-phenyl-2H,4H-pyrrolo[3,4-d][2]benzazepine-2-acetamide

A mixture of 2.3 g (6.5 mmole) of 8-chloro-6-phenyl-2H,4H-pyrrolo[3,4-d][2]benzazepine-2-acetic acid ethyl ester and 20 ml of methanolic ammonia (ca 20% v/v) was heated in an autoclave on a steambath overnight. The solvent was removed at reduced pressure to give a light yellow solid. Recrystallization from ethanol-hexane gave a white solid, mp 236°–237°.

EXAMPLE 23

α,4-Dichloro-2-(benzoyl)-benzenepropanenitrile

A solution of 92.7 g (0.4 mole) of 2-amino-5-chlorobenzophenone in 250 ml of acetonitrile was added to a mixture of 70 g (0.52 mole) of cupric chloride, 65 g (0.63 mole) of t-butylnitrile, 500 ml of acrylonitrile, and 500 ml of acetonitrile. When the addition was complete stirring at room temperature was continued for 2 hr. The mixture was diluted with 80 ml of 6 N hydrochloric acid and 1500 ml of water, extracted with ether and dried over anhydrous sodium sulfate. The ether solution was concentrated at reduced pressure to give a brown oil, which contained the end product and 2,5-dichlorobenzophenone. Trituration of the oil with a mixture of ether and petroleum ether gave the end product as a tan solid. Recrystallization of a small portion of the end product from a mixture of ether and petroleum ether gave pale yellow needles, mp 69°–71°.

EXAMPLE 24

α,4-Dichloro-2-(2-fluorobenzoyl)-benzenepropanenitrile

The preparation of α-4-dichloro-2-(2-fluorobenzoyl)-benzenepropanenitrile was conducted in the same manner as the preparation of a-4-dichloro-2-(benzoyl)-benzenepropanenitrile to give pale yellow prisms, mp 94°–95°.

EXAMPLE 25

α4-Dichloro-2-(2-chlorobenzoyl)-benzenepropanenitrile

The preparation of a 4-dichloro-2-(2-chlorobenzoyl)-benzenepropanenitrile was conducted in the same manner as the preparation of a-4-dichloro-2-(benzoyl)-benzenepropanenitrile to give off-white prisms, mp 102°–103°.

EXAMPLE 26

3-(2-Benzoyl-4-chlorobenzyl)-2-propanenitrile

A mixture of 50.9 g (0.188 mole) of a-4-dichloro-2-(benzoyl)-benzenepropanenitrile, 17 g (0.14 mole) of potassium carbonate, 50.9 g (0.5 mole) of potassium bicarbonate and 510 ml of dimethyl sulfoxide was stirred at room temperature for 48 hr. The mixture was diluted with 1.5 l of water, and the resulting precipitate was collected by filtration. Recrystallization from a mixture of methylene chloride and ether gave off-white prisms, mp 89°–91°.

EXAMPLE 27

8-Chloro-6-(2-fluorophenyl)-1-methyl-3-[(trichloromethyl)carbonyl]-2H,4H-pyrrolo[3,4-d][2]benzazepine A mixture of 3.4 g (11 mmole) of 8-chloro-6-(2-fluorophenyl)-1-methyl-2H,4H-pyrrolo[3,4-d][2]benzazepine, 2.6 g (14 mmole) of trichloroacetyl chloride, and 100 ml of methylene chloride was stirred at room temperature for 12 hr. The resulting precipitate was collected by filtration, resuspended in methylene chloride, and basified with ammonium hydroxide. The methylene chloride solution was separated, dried over anhydrous sodium sulfate, and concentrated at reduced pressure to give a (mp 222°–225°) colorless solid. A small portion was recrystallized from a mixture of methylene chloride and ether to give colorless prisms, mp 222°–223°.

EXAMPLE 28

8-Chloro-6-(2-fluorophenyl)-1-methyl-2H,4H-pyrrolo[3,4-d][2]benzazepine-3-carboxylic acid methyl ester A mixture of 3.0 g (6.4 mmole) of 8-chloro-6-(2-fluorophenyl)-1-methyl-3-[(trichloromethyl)carbonyl]-2H,4H-pyrrolo[3,4-d][2]benzazepine, 0.5 ml (2 mmole) of a 4 M methanol solution of sodium methoxide and 100 ml of methanol was heated to 40° for 30 min. The methanol solution was concentrated at reduced pressure, and the residue was partitioned between methylene chloride and water. The methylene chloride solution was dried with anhydrous sodium sulfate and concentrated at reduced pressure to give (mp 228°–231°) tan needles. Recrystallization from methylene chloride gave fine colorless needles, mp 229°–231°.

EXAMPLE 29

8-Chloro-6-(2-fluorophenyl)-N,1-dimethyl-2H,4H-pyrrolo[3,4-d][2]benzazepine-3-carboxamide A mixture of 1.0 g (2.1 mmole) of 8-chloro-6-(2-fluorophenyl)-1-methyl-3-[(trichloromethyl)carbonyl]-2H,4H-pyrrolo[3,4-d][2]benzazepine and 70 ml of methanol saturated with methylamine was heated in a bomb on a steam bath for 48 hr. The mixture was cooled, and the methanol was removed at reduced pressure to give a solid residue. The residue was partitioned between methylene chloride and water. The methylene chloride layer was separated, dried with anhydrous sodium sulfate, and concentrated at reduced pressure to give (mp 252°–255° C.) tan needles. Recrystallization from methylene chloride gave colorless needles, mp 266°–268° C.

EXAMPLE 30

8-Chloro-6-(2-fluorophenyl)-1-(2-propenyl)-2H,4H-pyrrolo[3,4-d][2]benzazepine and 8-chloro-6-(2-fluorophenyl)-3-(2-propenyl)-2H,4H-pyrrolo[3,4-d][2]benzazepine By means of a syringe 20 ml (12.5 mmole) of a 0.62 M tetrahydrofuran solution of lithium diisopropylamide was added dropwise to a solution of 3.1 g (9.6 mmole) of 8-chloro-6-(2-fluorophenyl)-2H,4H-pyrrolo[3,4-d][2]benzazepine in 75 ml of dry tetrahydrofuran which was cooled to −20° C. The solution was stirred at −20° C. for 5 minutes followed by the addition of 5.0 ml (55 mmole) of allyl bromide. The mixture was allowed to warm to room temperature and stirred for 2 hours. Water was added and the mixture extracted with ether. The ether solution was washed with water, dried over anhydrous sodium sulfate, and concentrated at reduced pressure to give an amber oil. Purification by column chromatography (silica gel, 70 g; eluent 5% ether in methylene chloride) gave the less polar compound. Recrystallization from a mixture of ether and petroleum ether gave cream prisms, mp 135°–140° C. (foams).

The methanesulfonate salt of 8-chloro-6-(2-fluorophenyl)-3-(2-propenyl)-2H,4H-pyrrolo[3,4-d][2]benzazepine was prepared by adding equimolar amounts of the base and methanesulfonic acid to methanol and isolated by precipitating the salt with the addition of ether. Recrystallization from a mixture of methanol and ether gave orange prisms, mp 243°–244° C.

The final compound to be eluted gave starting material (mp 226°–227° C.) which was identical to an authentic sample.

EXAMPLE 31

8-Chloro-6-(fluorophenyl)-2-(2-propenyl)-4H-pyrrolo[3,4-d][2]benzazepine

In one portion, 0.7 g (2.2 mmole) of 8-chloro-6-(2-fluorophenyl)-2H,4H-pyrrolo[3,4-d][2]benzazepine was added to a solution of 0.3 g (2.6 mmole) of potassium t-butoxide in 30 ml of dry dimethylformamide which was cooled to 0° C. After stirring for 15 minutes, 1.0 ml (11 mmole) of allyl bromide was added and the mixture was allowed to warm to room temperature. Water was added and the mixture was extracted with methylene chloride. The methylene chloride solution was washed with water, dried over anhydrous sodium sulfate, and concentrated at reduced pressure to give a yellow oil. Purification by column chromatography (silica gel, 20 g; eluent 5% ether in methylene chloride) gave a yellow oil. Crystallization from a mixture of ether and petroleum ether gave a tan solid (mp 100°–102° C.). Recrystallization from a mixture of ether and petroleum ether gave colorless prisms, mp 104°–106° C.

EXAMPLE 32

8-Chloro-6-(2-fluorophenyl)-2-methyl-2H,4H-pyrrolo[3,4-d][2]benzazepine

In one portion, 0.7 g (2.2 mmole) of 8-chloro-6-(2-fluorophenyl)-2H,4H-pyrrolo[3,4-d][2]benzazepine was added to a solution of 0.3 g (2.6 mmole) of potassium t-butoxide in 30 ml of dry dimethylformamide which was cooled to 0° C. After stirring for 15 minutes 1.0 ml (16 mmole) of methyl iodide was added, and the mixture was allowed to warm to room temperature. Water was added, and the mixture was extracted with methylene chloride. The methylene chloride solution was washed with water, dried over anhydrous sodium sulfate, and concentrated at reduced pressure to give a yellow oil. Purification by column chromatography (silica gel, 20 g; eluent 5% ether in methylene chloride) gave a tan solid (mp 142°–144° C.). Recrystallization from a mixture of ether and petroleum ether gave cream colored prisms, mp 144°–146° C.

EXAMPLE 33

4-[4-Chloro-2-(2-fluorobenzoyl)phenyl]-5-(2propenyl)-1H-pyrrole-3-carbonitrile

A mixture of 3.1 g (11 mmole) of 3-[2-(2-fluorobenzoyl)-4-chlorophenyl]-2-propenenitrile, 3.0 g (12 mmole) of 1-tosyl-3-butenyl-isocyanide[1], and 25 ml of dimethyl sulfoxide in 50 ml of ether was added dropwise to a suspension of 0.8 g (16.5 mmole) of 50% sodium hydride in mineral oil and 100 ml of ether. When the addition was complete stirring was continued for 2 hours. The mixture was diluted with water and the ether layer was separated. The aqueous solution was extracted with ether. The combined ether extracts were washed with water, dried over anhydrous sodium sulfate and concentrated at reduced pressure to give a dark oil. Purification by column chromatography (silica gel, 150 g; eluent 5% ether in methylene chloride) gave colorless needles, (mp 142°–144° C.). Recrystallization from a mixture of ether and petroleum ether gave colorless needles, mp 142°–144° C.

[1] A. M. van Leusen, R. J. Bouma and O. Possel, Tetrahedron Letters, 3487 (1975).

EXAMPLE 34

8-Chloro-6-(2-fluorophenyl)-1-(2-propenyl)2H,-4H-pyrrolo[3,4-d][2]benzazepine

A mixture of 0.7 g (2 mmole) of 4-[4-chloro-2-(2-fluorobenzoyl)phenyl-5-(2-propenyl)-1H-pyrrole-3-carbonitrile and 0.7 g (18 mmole) of lithium aluminum hydride in 50 ml of tetrahydrofuran was stirred at room temperature for 48 hours. The excess lithium aluminum hydride was discharged by the dropwise addition of a saturated aqueous solution of potassium sodium tartarate. The mixture was diluted with methylene chloride and the methylene chloride solution was separated, dried over anhydrous sodium sulfate and concentrated at reduced pressure to give 4-aminomethyl-4-{4-chloro-2-[(2-fluorophenyl)hydroxymethyl]phenyl}-2-(2-propenyl)-1H-pyrrole as a mixture due to restricted rotation and supported by thin layer chromatography and its nmr spectrum.

A mixture of 150 mg (0.4 mmole) of 4-aminomethyl-4-{4-chloro-2-[(2-fluorophenyl)hydroxymethyl]phenyl}-2-(2-propenyl)-1H-pyrrole and 0.6 g (7.3 mmole) of manganese dioxide in 30 ml of tetrahydrofuran was refluxed for 2 hours. The mixture was cooled and filtered over celite. The filtrate was concentrated at reduced pressure to give a red oil. Purification by column chromatography (silica gel, 10 g; eluent 5% ether in methylene chloride) gave the end product as a tan solid, (mp 212°–214° C.). Recrystallization from a mixture of ether and methylene chloride gave colorless prisms, mp 213°–215° C. which were identical in every respect to an authentic sample.

EXAMPLE 35

8-Chloro-6-(2-fluorophenyl)-1-methyl-2H,4H-pyrrolo[3,4-d][2]benzazepine

A mixture of 1.0 g (3 mmole) of 4-[4-chloro-3-(2-fluorobenzoyl)phenyl]-5-methyl-1H-pyrrole-3-carbonitrile and 1.0 g (26 mmole) of lithium aluminum hydride in 100 ml of tetrahydrofuran was stirred at room temperature for 24 hours. The excess lithium aluminum hydride was discharged by the dropwise addition of a saturated aqueous solution of potassium sodium tartarate. The mixture was diluted with methylene chloride and the methylene chloride solution was separated, dried over anhydrous sodium sulfate, and concentrated at reduced pressure to give 4-aminomethyl-3-{4-chloro-2-[(2-fluorophenyl)hydroxymethyl]phenyl}-2-methyl-1H-pyrrole a mixture due to restricted rotation and supported by thin layer chromatography and its nmr spectrum.

A mixture of 150 mg (0.43 mmole) of 4-aminomethyl-3-{4-chloro-2-[(2-fluorophenyl)hydroxymethyl]phenyl}-2-methyl-1H-pyrrole and 600 mg (7.3 mmole) of manganese dioxide in 30 ml of tetrahydrofuran was refluxed for 2 hours. The mixture was cooled and filtered over celite. The filtrate was concentrated at reduced pressure to give an amber oil. Purification by column chromatography (silica gel, 10 g; eluent 5% ether in methylene chloride) gave a cream colored solid. Recrystallization from ether gave colorless needles, mp 226°–227° which was identical in every respect to an authentic sample.

EXAMPLE 36

8-Chloro-6-(2-fluorophenyl)-1-methyl-3-(2-propynyl)-2H,4H-pyrrolo[3,4-d][2]benzazepine By means of a syringe 7 ml (4.2 mmole) of a 0.62 M tetrahydrofuran solution of lithium diisopropylamide was added dropwise to a solution of 1.3 g (4.0 mmole) of 8-chloro-6-(2-fluorophenyl)-1-methyl-2H,4H-pyrrolo[3,4-d][2]benzazepine in 30 ml of dry tetrahydrofuran which was cooled to −20° C. The solution was stirred at −20° C. for 5 minutes followed by the addition of 2.4 ml (25 mmole) of 80% propargyl bromide in toluene. The mixture was allowed to warm to room temperature and stirred for 2 hours. Water was added and the mixture was extracted with ether. The ether solution was washed with water, dried over anhydrous sodium sulfate, and concentrated at reduced pressure to give an amber foam. Purification by column chromatography (silica gel, 20 g; eluent 5% ether in methylene chloride) gave a foam. Crystallization from a mixture of ether and petroleum ether gave cream prisms, (mp 179°–180°).

EXAMPLE 37

| Item | Ingredients | TABLET FORMULATION (Wet granulation) | | | |
|---|---|---|---|---|---|
| | | mg/tablet | mg/tablet | mg/tablet | mg/tablet |
| 1. | 8-chloro-6-(2-chlorophenyl)-2H,4H—pyrrolo[3,4-D][2]benzazepine or 8-chloro-1-methyl-6-(2-fluorophenyl)-2H—pyrrolo[3,4-D][2]benzazepine | 1 | 5 | 10 | 25 |
| 2. | Lactose | 202 | 232 | 261 | 280 |
| 3. | Modified Starch | 25 | 35 | 45 | 55 |
| 4. | Pregelatinized Starch | 20 | 25 | 30 | 35 |
| 5. | Distilled Water q.s. | — | — | — | — |
| 6. | Magnesium Stearate | 2 | 3 | 4 | 5 |
| | Weight of tablet | 250 mg | 300 mg | 350 mg | 400 mg |

Procedure:
1. Mix Items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

Procedure:
1. Mix Items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 38

| Item | Ingredients | TABLET FORMULATION (Direct compression) | | | |
|---|---|---|---|---|---|
| | | mg/tablet | mg/tablet | mg/tablet | mg/tablet |
| 1. | 8-chloro-6-(2-chlorophenyl)-2H,4H—pyrrolo[3,4-D][2]benzazepine or 8-chloro-1-methyl-6-(2-fluorophenyl)-2H—pyrrolo[3,4-D][2]benzazepine | 1 | 5 | 10 | 25 |
| 2. | Lactose | 221 | 217 | 212 | 181 |
| 3. | Avicel | 45 | 45 | 45 | 55 |
| 4. | Direct Compression Starch | 30 | 30 | 30 | 35 |
| 5. | Magnesium Stearate | 3 | 3 | 3 | 4 |

TABLET FORMULATION (Direct compression) -continued

| Item | Ingredients | mg/tablet | mg/tablet | mg/tablet | mg/tablet |
|------|-------------|-----------|-----------|-----------|-----------|
|      | Weight of tablet | 300 mg | 300 mg | 300 mg | 300 mg |

Procedure:
1. Mix Item 1 with an equal amount of lactose. Mix well.
2. Mix with Items 3, and 4, and the remaining amount of Item 2. Mix well.
3. Add magnesium stearate and mix for 3 minutes.
4. Compress on a suitable press equipped with appropriate punches.

Procedure:
1. Mix Item 1 with an equal amount of lactose. Mix well.
2. Mix with Items 3, and 4, and the remaining amount of Item 2. Mix well.
3. Add magnesium stearate and mix for 3 minutes.
4. Compress on a suitable press equipped with appropriate punches.

EXAMPLE 39

CAPSULE FORMULATION

| Item | Ingredients | mg/tablet | mg/tablet | mg/tablet | mg/tablet |
|------|-------------|-----------|-----------|-----------|-----------|
| 1. | 8-chloro-6-(2-chloro-phenyl)-2H,4H—pyrrolo[3,4-D][2]benzazepine or 8-chloro-1-methyl-6-(2-fluorophenyl)-2H—pyrrolo[3,4-D][2]benzazepine | 1 | 5 | 10 | 25. |
| 2. | Lactose | 203 | 293.5 | 328 | 372.5 |
| 3. | Starch | 30 | 35 | 40 | 30 |
| 4. | Talc | 15 | 15 | 20 | 20 |
| 5. | Aerosol OT | 1 | 1.5 | 2 | 2.5 |
|   | Capsule fill weight | 250 mg | 350 mg | 400 mg | 450 mg |

Procedure:
1. Mill Items 1, 2, 3, and 5 in a suitable mixer. Mill.
2. Add talc and mix well.
3. Encapsulate on suitable equipment.

Procedure:
1. Mill Items 1, 2, 3, and 5 in a suitable mixer. Mill.
2. Add talc and mix well.
3. Encapsulate on suitable equipment.

EXAMPLE 40

4-[4-Chloro-2-(2-chlorobenzoyl)phenyl]-5-methyl-1H-pyrrole-3-carbonitrile (Product 1) and 6-chloro-8-(2-chlorophenyl)-1,8-dihydro-8-hydroxy-2-methylindeno[2,1-b]pyrrole-3-carbonitrile (Product 2)

A mixture of 33.9 g (0.11 mol) of 3-[2-(2-chlorobenzoyl)-4-chlorophenyl]-2-propenenitrile, 20 g (0.96 mol) of 1-tosylethyl isocyanide in a mixture of 150 ml of dimethyl sulfoxide and 190 ml of ether was added dropwise to a suspension of 4.6 g (0.1 mol) of a 50% mineral oil dispersion of sodium hydride in 100 ml of ether which was immersed in a room temperature water bath. Stirring at room temperature was continued for 2 hr. The mixture was diluted with 1.2 l of water and 40 ml of 1 N hydrochloric acid and extracted with methylene chloride. The methylene chloride solution was washed with water, dried over anhydrous sodium sulfate and concentrated at reduced pressure to give a dark green oil. Crystallization from a mixture of ether and petroleum ether gave Product 1 (mp 206°–208°) as tan crystals. Recrystallization from ether gave Product 1 as colorless crystals, mp 210°–211°.

A second crop of crystals which were Product 2 (mp 221°–225°) was obtained from ether. Recrystallization from ether gave Product 2 as pale yellow prisms, mp 232°–237°.

EXAMPLE 41

8-Chloro-6-(2-chlorophenyl)-1-methyl-2H,4H-pyrrolo[3,4-d][2]benzazepine

A mixture of 8.5 g (24 mmol) of 4-[4-chloro-2-(2-chlorobenzoyl)phenyl]-5-methyl-1H-pyrrole-3-carbonitrile, 1 spoonful of Raney nickel and 250 ml of glacial acetic acid was hydrogenated on a Parr apparatus at 55 psi overnight. The catalyst was removed by filtration and the acetic acid was removed at reduced pressure. The residue was diluted with water, basifified with concentrated ammonium hydroxide and the resulting precipitate was collected by filtration. The precipitate was dissolved in tetrahydrofuran, dried over anhydrous sodium sulfate and concentrated at reduced pressure. The residue was crystallized from a mixture of ether and petroleum ether to give off-white crystals (mp 219°–222°). Recrystallization from a mixture of ether and methylene chloride gave colorless crystals, mp 221°–225°.

EXAMPLE 42

8-Chloro-6-(2-chlorophenyl)-2-methyl-2H,4H-pyrrolo[3,4-d][2]benzazepine

The preparation of 8-chloro-6-(2-chlorophenyl)-2-methyl-2H,4H-pyrrolo[3,4-d][2]benzazepine was conducted in the same manner as the preparation of 8-chloro-6-(2-fluorophenyl)-2-methyl-2H,4H-pyrrolo[3,4-d][2]benzazepine (Example 32) to give colorless prisms, mp 167°–168°.

The methanesulfonate salt of 8-chloro-6-(2-chlorophenyl)-2-methyl-2H,4H-pyrrolo[3,4-d][2]benzazepine was prepared by adding equimolar amounts of the base compound and methanesulfonic acid to methanol and isolated by precipating the salt with the addition of ether. Recrystallization from a mixture of methanol and ether gave the methanesulfonate salt as orange prisms, mp 200°–203°.

EXAMPLE 43

8-Chloro-2-[2-(diethylamino)ethyl]-6-(2-fluorophenyl)-2H,4H-pyrrolo[3,4-d][2]benzazepine dihydrochloride In one portion 2.0 g (6.5 mmol) of 8-chloro-6-(2-fluorophenyl)-2H,4H-pyrrolo[3,4-d][2]benzazepine was added to 0.9 g (8 mmol) of potassium t-butoxide in 35 ml of dimethylformamide which was cooled to 0°. After stirring for 15 min, 3 ml (9 mmol) of a 3 M toluene solution of diethylaminoethyl chloride was added. The mixture was allowed to warm to room temperature and stir for 2 hr. The mixture was diluted with water and extracted with methylene chloride. The methylene chloride solution was washed with water, dried over anhydrous sodium sulfate and concentrated at reduced pressure. Purification of the residue by column chromatography (25 g, silica gel; eluent 4:1 methylene chloride:ether) gave an off-white solid, mp 110°–112°. The white solid was dissolved in 10 ml of 1.4 M methanolic hydrogen chloride and the solution was diluted with ether. The resulting precipitate was collected by filtration to give the dihydrochloride salt as an orange solid. Recrystallization from a mixture of methylene chloride and ether gave the dihydrochloride salt as orange crystals, mp 229°–231°.

EXAMPLE 44

8-Chloro-6-(2-fluorophenyl)-2H,4H-pyrrolo[3,4-d][2]benzazepine-2-acetic acid methyl ester In one portion 2.0 g (6.4 mmol) of 8-chloro-6-(2-fluorophenyl)-2H,4H-pyrrolo[3,4-d][2]benzazepine was added to a solution of 0.9 g (8 mmol) of potassium t-butoxide in 30 ml of dimethylformamide which was cooled to 0°. After stirring for 15 min, 0.7 ml (7.5 mmol) of methyl bromoacetate was added. The mixture was stirred for 5 min, diluted with water and extracted with ether. The ether solution was washed with water, dried over anhydrous sodium sulfate and concentrated at reduced pressure to dryness. Purification of the residue by column chromatography gave a pale yellow oil.

EXAMPLE 45

8-Chloro-6-(2-chlorophenyl)-2H,4H-pyrrolo[3,4-d][2]benzazepine-2-carboxylic acid methyl ester In one portion 6.0 g (18.3 mmol) of 8-chloro-6-(2-chlorophenyl)-2H,4H-pyrrolo[3,4-d][2]benzazepine was added to a solution of 3.0 g (26.5 mmol) of potassium t-butoxide in 50 ml of dimethylformamide which was cooled to 0°. When solution was complete 1.8 ml (2.3 g; 24.5 mmol) of methyl chloroformate was added and the resulting mixture was stirred for 15 min. The mixture was diluted with 150 ml of water and the resulting precipitate was collected by filtration. The precipitate was dissolved in methylene chloride and washed with water. The methylene chloride solution was dried over anhydrous sodium sulfate and concentrated at reduced pressure. The residue crystallized from ether to give an off-white solid. Recrystallization from a mixture of methylene chloride and ether gave off-white fine needles, mp 185°–186° (dec.).

EXAMPLE 46

8-Chloro-6-(2-fluorophenyl)-2-methyl-2H,6H-pyrrolo[3,4-d][2]benzazepine

In one portion 3.0 g (9.5 mmol) of 8-chloro-6-(2-fluorophenyl)-2H,4H-pyrrolo[3,4-d][2]benzazepine was added to a mixture of 1.5 g (13.2 mmol) of potassium t-butoxide and 100 ml of dimethyl sulfoxide which was cooled in a water bath to 15°. The mixture was stirred for 10 min followed by the addition of 4.0 ml (64 mmol) of methyl iodide. After stirring for 30 min the mixture was diluted with water and extracted with ether. The ether solution was washed with water, dried over anhydrous sodium sulfate and concentrated at reduced pressure. The solid residue was recrystallized from a mixture of ether and methylene chloride to give colorless needles, mp 215°–217°.

The mother liquors, by thin layer chromatography contained a mixture of the end product and the isomeric compound 8-Chloro-6-(2-fluorophenyl)-2-methyl-2H,4H-pyrrolo[3,4-d][2]benzazepine. No effort was made in the purification of the mixture.

EXAMPLE 47

8-Chloro-6-(2-fluorophenyl)-2,5-dimethyl-2H,4H-pyrrolo[3,4-d][2]benzazepin-5-ium iodide In one portion 2.0 g (6.4 mmol) of 8-chloro-6-(2-fluorophenyl)-2H,4H-pyrrolo[3,4-d][2]benzazepine was added to a solution of 0.9 g (8.0 mmol) of potassium t-butoxide in 30 ml of dimethylformamide which was cooled to 0°. After stirring for 5 min 2.0 ml (32 mmol) of methyl iodide was added and stirring was continued for 1 hr. Water was added and the mixture was extracted with ether. The ether solution was washed with water, dried over anhydrous sodium sulfate and concentrated at reduced pressure to give a waxy solid. Purification by column chromatography (silica gel; eluent 5% ether in methylene chloride) gave colorless crystals, mp 142°–143°.

The aqueous dimethylformamide solution was extracted with methylene chloride. The methylene chloride solution was washed with water, dried over anhydrous sodium sulfate and concentrated at reduced pressure to dryness. Trituration of the residue with a mixture of methanol and ether gave the end product as an orange solid. Recrystallization from a mixture of methanol and ether gave orange prisms, mp 228°–231°.

EXAMPLE 48

8-Chloro-6-(2-chlorophenyl)-2,5-dimethyl-2H,4H-pyrrolo[3,4-d][2]benzazepin-5-ium iodide In one portion 3.0 g (9.2 mmol) of 8-chloro-6-(2-chlorophenyl)-2H,4H-pyrrolo[3,4-d][2]benzazepine was added to a solution of 1.35 g (12 mmol) of potassium t-butoxide in 30 ml of dimethylformamide which was cooled to 0°. After stirring for 15 min 5 ml (80 mmol) of methyl iodide was added. The mixture was warmed to room temperature and stirred for 4 hr. The mixture was diluted with water and extracted with methylene chloride. The methylene chloride solution was washed with water, dried over anhydrous and sodium sulfate and concentrated at reduced pressure to a red oil. Crystallization was induced by the addition of a small amount of methanol to give a yellow solid. Recrystallization from a mixture of methanol and ether gave fine orange needles, mp 195°–197°.

EXAMPLE 49

8-Chloro-6-(2-chlorophenyl)-2,5-dimethyl-5,6-dihydro-2H,4-pyrrolo[3,4-d][2]benzazepine Portionwise 0.2 g (52 mmol) of sodium borohydride was added to a solution of 3.0 g (6.3 mmol) of 8-chloro-6-(2-chlorophenyl)-2,5-dimethyl-2H,4H-pyrrolo[3,4-d][2]benzazepin-5-ium iodide in 50 ml of methanol which was cooled to 0°. The mixture was stirred at 0° for 20 min followed by the removal of the methanol at reduced pressure. The residue was partitioned between methylene chloride and water. The methylene chloride solution was washed with water and saturated aqueous sodium chloride, dried over anhydrous sodium sulfate, and concentrated at reduced pressure to give a pale yellow oil. Crystallization from ether gave colorless crystals, mp 154°–155°.

EXAMPLE 50

8-Chloro-6-(2-fluorophenyl)-2H,4H-pyrrolo[3,4-d][2]benzazepine-2-ethanol

A solution of 2.3 g (6.0 mmol) of 8-chloro-6-(2-fluorophenyl)-2H,4H-pyrrolo[3,4-d][2]benzazepine-2-acetic acid methyl ester in 25 ml of tetrahydrofuran was added dropwise to a solution of 0.5 g (13 mmol) of lithium aluminum hydride in 30 ml of tetrahydrofuran which was cooled to −78°. The reaction was allowed to warm to 0° and was stirred for 2 hr. The excess lithium aluminum hydride was discharged by the addition of 0.6 ml of water, 0.6 ml of 10% sodium hydroxide and 2.0 ml of water. The resulting precipitate was removed by filtration and the filtrate was concentrated at reduced pressure to dryness. The residue crystallized from ether to give a white solid. Recrystallization from a mixture of ether and petroleum ether gave colorless prisms, mp 145°–147°.

EXAMPLE 51

8-Chloro-6-(2-chlorophenyl)-5,6-dihydro-2H,4H-pyrrolo[3,4-d][2]benzazepine

In five portions 0.5 g (7.9 mmol) of sodium cyanoborohydride and 35 ml of a 1 M methanol solution of methanesulfonic acid was added over 4 hr to a solution of 2.0 g (6.1 mmol) of 8-chloro-6-(2-chlorophenyl)-2H,4H-pyrrolo[3,4-d][2]benzazepine in 50 ml of methanol which was cooled to 0°. When the addition was complete stirring was continued overnight at room temperature. The solution was basified with 40% aqueous sodium hydroxide and diluted with water. The resulting precipitate was collected by filtration to give a white solid. Recrystallization from a mixture of ether and methylene chloride gave colorless crystals, mp 211°–212°.

EXAMPLE 52

1-[8-Chloro-6-(2-fluorophenyl)-2H,4H-pyrrolo[3,4-d][2]benzazepin-3-yl]-2,2,2-trichloroethanone A mixture of 0.7 g (2.2 mmol) of 8-chloro-6-(2-fluorophenyl)-2H,4H-pyrrolo[3,4-d][2]benzazepine and 2.0 ml (18 mmol) of trichloroacetyl chloride in 20 ml of methylene chloride was refluxed for 7 days. The resulting precipitate was collected by filtration and partitioned between methylene chloride and saturated aqueous sodium bicarbonate. The methylene chloride solution was dried over anhydrous sodium sulfate and concentrated at reduced pressure to give a white solid mp 240°–245° (dec).

EXAMPLE 53

8-Chloro-6-(2-chlorophenyl)-2H,4H-pyrrolo[3,4-d][2]benzazepine-3-carboxaldehyde

A solution of 3.0 ml (33 mmol) of phosphorous oxychloride in 20 ml of methylene chloride was added dropwise to a solution of 3.0 g (9.1 mmol) of 8-chloro-6-(2-chlorophenyl)-2H,4H-pyrrolo[3,4-d][2]benzazepine in 40 ml of dimethylformamide which was cooled to 0°. Stirring at 0° was continued for 2 hr. The mixture was poured into a saturated solution of aqueous sodium carbonate and extracted with methylene chloride. The methylene chloride solution was washed with water, dried over anhydrous sodium sulfate and concentrated at reduced pressure to dryness. Purification by column chromatography (silica gel, 100 g; eluent, 50% (v/v) ethyl acetate in methylene chloride) gave a light pink solid, mp 270°–274°. Recrystallization from a mixture of ethyl acetate and methylene chloride gave peach colored prisms, mp 276°–277°.

EXAMPLE 54

8-Chloro-6-(2-chlorophenyl)-2H,4H-pyrrolo[3,4-d][2]benzazepine-3-carboxylic acid hemietherate A solution of 1.5 g (9.5 mmol) of potassium permanganate in 150 ml of 50% aqueous acetone was added dropwise to a solution of 1.6 g (4.5 mmol) of 8-chloro-6-(2-chlorophenyl)-2H,4H-pyrrolo[3,4-d][2]benzazepine-3-carboxaldehyde in 100 ml of acetone. After 2.5 hr the mixture was diluted with a saturated aqueous solution of sodium bisulfite, neutralized with the addition of acetic acid and extracted with methylene chloride. The methylene chloride solution was dried over anhydrous sodium sulfate and concentrated at reduced pressure to dryness. Trituration of the residue with methylene chloride gave yellow crystals, mp 216°–218°. Recrystallization from a mixture of ethanol and ether gave yellow prisms, mp 252°–254° (dec).

EXAMPLE 55

8-Chloro-6-(2-chlorophenyl)-2H,4H-pyrrolo[3,4-d][2]benzazepine-3-carboxylic acid methyl ester methanesulfonate A solution of 0.8 g (2.2 mmol) of crude 8-chloro-6-(2-chlorophenyl)-2H,4H-pyrrolo[3,4-d][2]benzazepine-3-carboxylic acid in 20 ml of a 50% mixture of tetrahydrofuran and methylene chloride was added 20 ml of a 1 M etherial solution of diazomethane. The excess diazomethane was discharged with the addition of acetic acid. The organic solution was washed with saturated aqueous sodium bicarbonate, dried over anhydrous sodium sulfate and concentrated at reduced pressure to dryness. The residue was purified by column chromatography (silica gel, 20 g; eluent, 20% ether in methylene chloride) to give a pale yellow oil. The oil was dissolved in methanol containing 1 ml of a 1 M methanol solution of methanesulfonic acid and the salt was isolated by the addition of ether. Recrystallization from a mixture of methanol and ether gave the methanesulfonate salt as yellow crystals, mp 273°–274° (dec.).

EXAMPLE 56

8-Chloro-6-(2-chlorophenyl)-1-methyl-2H,4H-pyrrolo[3,4-d][2]benzazepine-3-carboxaldehyde By means of a syringe 0.6 ml (6.5 mmol) of phosphorous oxychloride was added to a solution of 0.7 g (2.0 mmol) of 8-chloro-6-(2-chlorophenyl)-1-methyl-2H,4H-pyrrolo[3,4-d][2]benzazepine in 8 ml of dimethylformamide which was cooled to 0°. The mixture was stirred at 0° for 1 hr, poured into 50 ml of saturated aqueous sodium carbonate and extracted with methylene chloride. The methylene chloride solution was washed with water, dried over anhydrous sodium sulfate and concentrated at reduced pressure to give a red amorphous solid. Purification by column chromatography (silica gel, 20 g; 4% ether in methylene chloride, eluent) gave an off-white solid. Recrystallization from a mixture of methylene chloride and ethyl acetate gave off-white crystals, mp 274°–276°.

EXAMPLE 57

8-Chloro-6-(2-chlorophenyl)-3-(hydroxymethyl)-1-methyl-2H,4H-pyrrolo[3,4-d][2]benzazepine In one portion 0.2 g (5.2 mmol) of sodium borohydride was added to 0.9 g of 8-chloro-6-(2-chlorophenyl)-2H,4H-pyrrolo[3,4-d][2]benzazepine-3-carboxaldehyde in 20 ml of methanol which was cooled to 0°. After stirring at 0° for 30 min, water was added and the resulting precipitate was collected by filtration to give a tan amorphous solid (mp 170°–180° dec.). All attempts to purify this product led to the introduction of impurities by decomposition.

EXAMPLE 58

8-Chloro-6-(2-chlorophenyl)-2H,4H-pyrrolo[3,4-d][2]benzazepine-5-oxide

Method A. A solution of 4.0 g (20 mmol) of 85% m-chloroperbenzoic acid in 50 ml of methylene chloride was added dropwise to a solution of 5.0 g (15 mmol) of 8-chloro-6-(2-chlorophenyl)-2H,4H-pyrrolo[3,4-d][2]benzazepine in 250 ml of methylene chloride which was cooled to 0°. The mixture was stirred at 0° for 2 hr and washed with saturated aqueous sodium bicarbonate, water and saturated aqueous sodium sulfate and concentrated at reduced pressure to give an oil. Crystallization from ethyl acetate gave a cream colored solid. Recrystallization from a mixture of methylene chloride and ether gave fine colorless needles, mp 233°–235°.

Method B. A mixture of 1.0 g (2.4 mmol) of 8-chloro-6-(2-chlorophenyl)-2H,4H-pyrrolo[3,4-d][2]benzazepine-2-carboxylic acid methyl ester 5-oxide and 2.5 ml of 3 N aqueous sodium hydroxide in a mixture of 10 ml of methanol and 50 ml of tetrahydrofuran was stirred at room temperature for 20 min. The mixture was concentrated at reduced pressure and the residue was partitioned between water and methylene chloride. The methylene chloride solution was washed with water, dried over anhydrous sodium sulfate, and concentrated at reduced pressure. The residue was triturated with a mixture of tetrahydrofuran and ether to give an off-white solid, mp 239°–240°. Recrystallization from a mixture of ether and methylene chloride gave fine colorless needles, mp 241°–242°. Spectroscopic analysis clearly show the products as identical although the melting points differ.

EXAMPLE 59

8-Chloro-6-(2-chlorophenyl)-2H,4H-pyrrolo[3,4-d][2]benzazepine-2-carboxylic acid methyl ester 5-oxide A mixture of 4.2 g (11 mmol) of 8-chloro-6-(2-chlorophenyl)-2H,4H-pyrrolo[3,4-d][2]benzazepine-2-carboxylic acid methyl ester and 3.15 g (14.5 mmol) of m-chloroperbenzoic acid in 100 ml of methlene chloride was stirred at 0° for 2.5 hr. The mixture was washed with saturated aqueous sodium bicarbonate and saturated aqueous sodium chloride, dried over anhydrous sodium sulfate and concentrated at reduced pressure to dryness. The residue was crystallized from ether to give a white solid, mp 224°–226°. Recrystallization from a mixture of ether and methylene chloride gave colorless prisms, mp 226°–227°.

EXAMPLE 60

4-(Acetyloxy)-8-chloro-6-(2-chlorophenyl)-2H,4H-pyrrolo[3,4-d][2]benzazepine-2-carboxylic acid methyl ester A mixture of 7.6 g (19 mmol) of 8-chloro-6-(2-chlorophenyl)-2H,4H-pyrrolo[3,4-d][2]benzazepine-2-carboxylic acid methyl ester 5-oxide and 200 ml of acetic anhydride was stirred at 70° for 12 hr and at 105° for 5 hr. The acetic anhydride solution was concentrated at reduced pressure. The residue was dissolved in methylene chloride and washed with saturated aqueous sodium bicarbonate and saturated aqueous sodium chloride. The methylene chloride solution was dried over anhydrous sodium sulfate and concentrated at reduced pressure to give an oil. Purification by column chromatography (50 g, neutral alumina; 5% ether in methylene chloride, eluent) gave a tan solid, mp 175°–177°. Recrystallization from ether gave an off-white solid, mp 177°–178°.

EXAMPLE 61

8-Chloro-6-(2-chlorophenyl)-4-methoxy-2H,4H-pyrrolo[3,4-d][2]benzazepine

A mixture of 1.0 g (2.2 mmol) of 4-(acetyloxy)-8-chloro-6-(2-chlorophenyl)-2H,4H-pyrrolo[3,4-d][2]benzazepine-2-carboxylic acid methyl ester and 2.5 ml of 3 N aqueous sodium hydroxide solution in a mixture of 25 ml of tetrahydrofuran and 10 ml of methanol was stirred at 0° for 30 min. The mixture was diluted with water and extracted with methylene chloride. The methylene chloride solution was washed with saturated aqueous sodium chloride, dried over anhydrous sodium sulfate and concentrated at reduced pressure to dryness. The residue was triturated with a mixture of ether and methylene chloride to give a cream colored solid, mp 215°–218°. Recrystallization from a mixture of tetrahydrofuran and hexane gave tan prisms, mp 221°–224°.

EXAMPLE 62

8-Chloro-2-methyl-4-methoxy-6-(2-chlorophenyl)-2H,4H-pyrrolo[3,4-d][2]benzazepine In one portion 1.0 g (2.8 mmol) of 8-chloro-6-(2-chlorophenyl)-4-methoxy-2H,4H-pyrrolo[3,4-d][2]benzazepine was added to a solution of 0.35 g (3.0 mmol) of potassium t-butoxide in 20 ml of dimethylformamide which was cooled to 0°. After stirring for 15 min, 0.3 ml (4.8 mmol) of methyl iodide was added. The mixture was stirred for 5 min, diluted with water and extracted with ether. The ether solution was washed with water, dried over anhydrous sodium sulfate, and concentrated at reduced pressure to give a pale yellow oil. Purification by column chromatography (silica gel, 25 g; 5% ether in methylene chloride, eluent) gave an off-white solid, mp 128°-130°. Recrystallization from a mixture of ether and petroleum ether gave off-white prisms, 128°-130°.

EXAMPLE 63

3-[2-(2-Fluorobenzoyl)-4-chlorophenyl]-2-propenenitrile

A solution of 5.0 g (14 mmol) of 5-chloro-2'-fluoro-2-iodobenzophenone, 2 ml (14.3 mmol) of triethylamine, 2 ml(30 mmol) of acrylonitrile and 35 mg (1.5 mmol) of palladium acetate was refluxed under an atmosphere of argon for 16 hr. The mixture was diluted with 100 ml of 1 N hydrochloric acid and the resulting precipitate was collected by filtration. The precipitate was washed with ether and air dried to give an off-white solid, mp 130°-133°.

EXAMPLE 64

8-Chloro-2-[2-(dimethylamino)ethyl]-6-(2-fluorophenyl)-2H,4H-pyrrolo[3,4-d][2]benzazepine dihydrochloride The preparation of 8-chloro-2-[2-(dimethylamino)ethyl]-6-(2-fluorophenyl)-2H,4H-pyrrolo[3,4-d][2]benzazepine dihydrochloride was conducted in the same manner as the preparation of 8-chloro-2-[3-(dimethylamino)propyl]-6-(2-fluorophenyl)-2H,4H-pyrrolo[3,-4-d][2]benzazepine dihydrochloride to give the product as yellow crystals, mp 264°-266°.

EXAMPLE 65

8-Chloro-2-[3-(dimethylamino)propyl]-6-(2-fluorophenyl)-2H,4H-pyrrolo[3,4-d][2]benzazepine dihydrochloride In one portion 1.5 g (4.8 mmol) of 8-chloro-6-(2-fluorophenyl)-2H,4H-pyrrolo[3,4-d][2]benzazepine was added to a solution of 0.6 g (5.3 mmol) of potassium t-butoxide in 25 ml of dimethylformamide which was cooled to 0°. After stirring for 15 min, 5.2 ml (10.4 mmol) of a 2 M toluene solution of dimethylaminopropyl chloride was added. The mixture was warmed to room temperature and stirred for 4 hr. The mixture was diluted with water and extracted with methylene chloride. The methylene chloride solution was washed with water, dried over anhydrous sodium sulfate and concentrated at reduced pressure. Purification of the residue by column chromatography (silica gel, 25 g; eluents, 4:1 ration of methylene chloride:ether followed by 1:2:7 ratio of methanol:ether:methylene chloride) gave a colorless oil. The oil was dissolved in an excess of methanolic hydrogen chloride and the solution was concentrated at reduced pressure. Crystallization of the residue from a mixture of isopropanol and ether gave an orange solid, mp 258°-260°.

EXAMPLE 66

8-Chloro-2-[2-(diethylamino)ethyl]-6-(2-chlorophenyl)-2H,4H-pyrrolo[3,4-d][2]benzazepine In one portion 2.1 g (6.4 mmol) of 8-chloro-6-(2-chlorophenyl)-2H,4H-pyrrolo[3,4-d][2]benzazepine was added to a solution of 0.8 g (7.0 mmol) of potassium t-butoxide in 35 ml of dimethyl formamide which was cooled to 0°. After stirring for 15 min 2.5 ml (7.5 mmol) of a 3 M toluene solution of diethylaminoethyl chloride was added. The mixture was warmed to room temperature and stirred for 3 hr. The mixture was diluted with water and extracted with methylene chloride. The methylene chloride solution was washed with water, dried over anhydrous sodium sulfate and concentrated at reduced pressure. Purification of the residue by column chromatography (25 g, silica gel; eluent 4:1 methylene chloride:ether) gave an off-white solid, mp 130°-131°.

EXAMPLE 67

8-Chloro-2-[2-(diethylamino)ethyl]-5,6-dihydro-6-(2-fluorophenyl)-2H,4H-pyrrolo[3,4-d][2]benzazepine dihydrochloride Portionwise over a 30 min. period, 0.3 g (5.3 mmol) of sodium cyanoborohydride was added to a solution of 0.3 g (0.75 mmol) of 8-chloro-2-[2-(diethylamino)ethyl]-6-(2-fluorophenyl)-2H,4H-pyrrolo[3,4-d][2]benzazepine dihydrochloride. During the course of the reaction a total of 6.0 mL (8.4 mmol) of a 1.4 M methanol solution of hydrogen chloride was added to maintain an acidic pH. The methanol was removed at reduced pressure and the residue partitioned between aqueous ammonium hydroxide and ether. The ether solution was dried over anhydrous sodium sulfate and concentrated at reduced pressure to dryness. The residue was dissolved in an excess of methanolic hydrogen chloride and 50 mL of isopropanol. Concentration of the solution at reduced pressure gave the product as a white solid. Recrystallization from a mixture of ether and methanol gave the product as colorless needles, mp 265°-270° C. (dec.).

What is claimed:

1. The compound of the formula

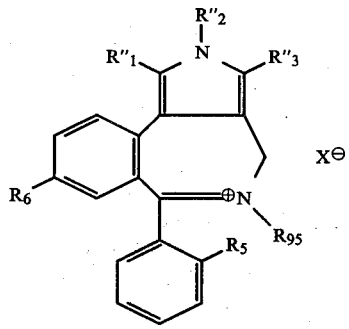

wherein $R_1''$ and $R_3''$ are selected from the group consisting of hydrogen, lower alkyl, $C_3$ to $C_7$ alkenyl and $C_3$ to $C_7$ alkynyl; $R_2''$ is hydrogen, lower alkyl, $C_3$ to $C_7$ alkenyl, $C_3$ to $C_7$ alkynyl, the group

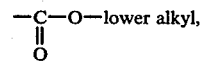

the group $-C_7$ to $C_6$ lower alkyl-$C_y$-$R_{21}$, or hydroxy $C_2$ to $C_7$alkyl; $R_{95}$ is lower alkyl; $R_5$ is hydrogen or halogen; $R_6$ is halogen; $R_{21}$ is hydroxy, lower alkoxy, amino or amino which is mono- or di-substituted by lower alkyl"and $X^\ominus$ is the anion of an organic or mineral acid.

2. A compound of claim 1: 8-chloro-6-(2-fluorophenyl)-2,5-dimethyl-2H,4H-pyrrolo [3,4-d][2]benzazepin-5-ium iodide.

3. A compound of claim 1: 8-chloro-6-(2-chlorophenyl)-2,5-dimethyl-2H,4H-pyrrolo [3,4-d][2]benzazepin-5-ium iodide.

* * * * *